United States Patent
Kranz et al.

(10) Patent No.: US 6,894,272 B2
(45) Date of Patent: May 17, 2005

(54) DEVICE FOR SIMULTANEOUSLY CARRYING OUT AN ELECTROCHEMICAL AND A TOPOGRAPHICAL NEAR-FIELD MICROSCOPY

(75) Inventors: Christine Kranz, Atlanta, GA (US); Boris Mizaikoff, Atlanta, GA (US); Alois Lugstein, Vienna (AT); Emmerich Bertagnolli, Vienna (AT)

(73) Assignee: Innovationsagentur Gesellschaft mbH, Vienna (AT)

( * ) Notice: Subject to any disclaimer, the term of this patent is extended or adjusted under 35 U.S.C. 154(b) by 34 days.

(21) Appl. No.: 10/297,627
(22) PCT Filed: Jun. 11, 2001
(86) PCT No.: PCT/AT01/00192

§ 371 (c)(1),
(2), (4) Date: Jun. 18, 2003

(87) PCT Pub. No.: WO01/94877

PCT Pub. Date: Dec. 13, 2001

(65) Prior Publication Data

US 2004/0004182 A1 Jan. 8, 2004

(51) Int. Cl.⁷ .............................................. G01N 23/00
(52) U.S. Cl. ...................... 250/234; 250/306; 250/307; 73/105
(58) Field of Search ............................. 250/234, 216, 250/306, 307, 201.3; 73/105

(56) References Cited

U.S. PATENT DOCUMENTS 5,936,237 A 8/1999 Van der Weide ............ 250/234
6,002,131 A * 12/1999 Manalis et al. ............. 250/306
6,703,614 B1 * 3/2004 Stifter et al. ................ 250/306

FOREIGN PATENT DOCUMENTS

EP 0027517 4/1981

OTHER PUBLICATIONS

Bard et al., "Chemical imaging of surfaces with the scanning electrochemical microscope," *Science*, 254:68–74, 1991.
Borgwarth et al., "Scanning electrochemical microscopy: a new scanning mode based on convective effects," *Berichte Der Bunsen–Gesellschaft—Physical Chemistry Chemical Physics*, 98:1317–1321, 1994.
Bottomley, "Scanning probe microscopy," *Anal. Chem*, 70:452R–475R, 1998.
James et al., "Scanning electrochemical microscopy with simultaneous independent topography," *J. Electrochem. Soc.*, 145(4):L64–L66, 1998.
Jones et al., "In situ observation of the surface process involved in dissolution from the (010) surface of potassium ferrocyanide trihydrate in aqueous solution using an integrated electrochemical—atomic force microscope," *J. Phys. Chem.*, 104:2351–2359, 2000.

(Continued)

Primary Examiner—Kevin Pyo
(74) Attorney, Agent, or Firm—Fulbright & Jaworski LLP

(57) ABSTRACT

A device for simultaneously carrying out an electrochemical and a topographical near field microscopy is described, which device comprises a region for topographical near field measurement and a region for electrochemical near field measurement, with the region for topographical near field measurement extending completely as far as to the immediate tip of the arrangement, characterized in that the region for electrochemical near field measurement starts at a defined distance from the immediate tip.

19 Claims, 19 Drawing Sheets

OTHER PUBLICATIONS

Jones et al., "Simultaneous topographical and amperometric imaging of surfaces in air: towards a combined scanning force—scanning electrochemical microscope (SF–SECM)," *Electrochemistry Communications*, 1:55–60, 1999.

Kwak and Bard, "Scanning electrochemical microscopy. Theory of the Feedback mode," 61:1221–1227, 1989.

Ludwig et al., "Topography feedback mechanism for the scanning electrochemical microscope based on hydrodynamic forces between tip and sample," *Rev. Sci. Instrum.*, 66(4):2857–2860, 1995.

Macpherson and Unwin, "Combined scanning electrochemical—atomic force microscopy," *Anal. Chem.*, 72:276–285, 2000.

Macpherson et al., "In–situ imaging of ionic crystal dissolution using an integrated electrochemical/AFM probe," *J. Am. Chem. Soc.*, 118:6445–6452, 1996.

Matsui and Ochiai, "Focused ion beam applications to solid state devices," *Nanotechnology*, 7:247–258, 1996.

Mirkin et al., "Scanning electrochemical microscopy. Part 13. Evaluation of the tip shapes of nanometer size microelectrodes," *J. Electroanal. Chem.*, 328:47–62, 1992.

Wipf and Bard, "Scanning electrochemical microscopy. 15. Improvements in imaging via tip–position modulation and lock–in detection," *Anal. Chem.*, 64: 1362–1367, 1992.

* cited by examiner (a)

(b)

(a)

(b)　　　　　　　(c)

(a)

(b)          (c)

DEVICE FOR SIMULTANEOUSLY CARRYING OUT AN ELECTROCHEMICAL AND A TOPOGRAPHICAL NEAR-FIELD MICROSCOPY

This application is a U.S. national phase application under 35 U.S.C. § 371 of PCT Application No. PCT/AT01/00192 filed Jun. 11, 2001, which claims priority to Austrian Application No. A 1012/2000 filed Jun. 9, 2000.

The present invention relates to a device for simultaneously carrying out an electrochemical and a topographical near field microscopy.

The utilization of ultramicroelectrodes for the laterally resolved characterization of sample surfaces provides quantitative and semi-quantitative data on parameters such as surface activity/surface reactivity, on the kinetics of heterogeneous as well as homogeneous electron-transfer reactions, on corrosion processes, on the activity of biological components and systems (e.g. the quantitation of enzyme activities, the study of substance transport phenomena on membranes, tissues and tissue parts, metabolic activities of individual cells, cell groups and cell clusters, as well as organ parts and organs), and can also be applied to the large field of the laterally resolved surface modification by means of etching (removal of material) or deposition (application of material).

A prerequisite for this is, however, an exact, reproducible control of the distance between the ultramicroelectrode and the sample in the range of a few electrode radii. By reacting the dissolved redox-active substance at the microelectrode, a diffusion-controlled current occurs due to the hemispheric diffusion to the microelectrode (FIG. 1($b$)). If the microelectrode is approached to the sample surface in the range of a few electrode radii, the field of diffusion is disturbed. If the sample surface is, e.g., conductive or chemically active, the redox-active substance can be recycled at the sample surface, resulting in a rise of the Faraday current (FIG. 1($a$)). If the microelectrode is approached to, e.g., a non-conductive or chemically inert sample surface in the range of a few electrode radii, the sample surface blocks diffusion to the microelectrode, resulting in a reduced Farady current (FIG. 1($c$)). This sample-dependent disturbance of the field of diffusion may be described theoretically via diffusion equations. The numerical solution of these differential equations yields the following approximation (cf. Mirkin et al., J. Electroanal. Chem., 328 (1992), 47–62):

Conductor:

$$i_T(L)/i_{T,\infty}=0.68+0.78377/L+0.3315\exp(-1.0672/L)$$

Isolator:

$$i_T(L)/i_{T,\infty}=1/[0.292+1.5151/I+0.6553\exp(-2.4035/L)]$$

$$L=d/r \quad \text{(Equation 1)}$$

with: d: distance between electrode and sample, and r: radius of microelectrode.

Accordingly, for improving the sensitivity and the dynamic range, a relatively small working distance is suitable which, however, is influenced by the properties, such as, e.g., the conductivity or the chemcial activity. In constant height mode, this harbors the risk of a collision between the microelectrode and the sample, if the working distance is chosen too short (FIG. 2). Therefore, knowing the absolute working distance and keeping the same constant is desirable.

So far, in most applications described in the literature, the change in the Farady current in the near field range measured on the microelectrode is utilized for positioning (cf. Bard et al., Science, 254 (1991), 68–74). By analysing the approximation curves, the distance between sample and microelectrode is determined. Since, however, in the real experiment, one can neither start out with an ideal electrode geometry (particularly if the electrodes become very small), nor from an ideally parallel arrangement, the distance between ultramicroelectrode and surface can be determined merely approximately.

Since in the conventional experiment the ultramicroelectrode does not only follow the topographical realities, the image obtained of the surface represents an overlaying of the influences, in particular of the electrochemical activity and the distance between the sample surface and the probe on the measured Faraday current at the ultramicroelectrode (FIG. 2).

With an ultramicroelectrode diameter in the range of 1–10 mm and a planar sample, this will only mean a conditional limitation of the imaging quality. These overlaying influences, however, rise proportionally to the decrease of the (electro)-active probe area. Therefore, an image of the surface in a constant height mode is only possible if the distance change (e.g. by the topography of the sample) or a tilting of the sample does not exceed the allowable working distance.

Since a marked improvement in the resolution can only be obtained by using smaller electrodes (<1 μm diameter), an alternative distance control must be used.

First approaches to solve this problem are based on a vertical modulation of the electrode, on the one hand, so as to allow for a differentiation between conductive regions with a current increase and non-conductive regions with a current decrease (cf. Wipf et al., Anal. Chem. 64 (1992), 1362–1367). By a logic circuit, the microelectrode can be guided to follow the topography, yet not in the border regions between conductive and non-conductive. On the other hand, the distance control is based on convective effects which, if the probe is quickly moved perpendicularly towards the surface, will lead to changes in the current (cf. Borgwarth et al., Ber. Bunsenges. Phys. Chem. 98 (1994), 1317).

Both methods are, however, still based on a current-dependent signal, and the distance between probe and sample cannot be exactly determined from the approximate curves.

On the other hand, a current-independent height control based on the detection of shearing forces (shear force mode), as has already been used in the scanning near field optical microscopy, could be successfully used for the positioning of microelectrodes (Ludwig et al., Rev. Sci. Instr. 66 (1995), 2857–2860). The basis of the shearing-force-based height control is the stimulation of the microelectrode to horizontal oscillations in parallel to the surface by means of a piezo-element, and the detection of the oscillation damping due to hydrodynamic effects if the probe is approached to the sample surface.

In U.S. Pat. No. 5,936,237, a combination of electromagnetic and topographical near field microscopy is described. An electrochemical near field microscopy is, however—simply due to the completely different local interactions on which it is based and the structural measures involved for the electrochemical measurement, on the one hand, and the electromagnetic measurement, on the other hand—not possible with the device described therein.

Ludwig et al. describe a current-independent height control based on an optical detection principle. A laser beam focussed on the tip of the probe produces a Fresnel diffraction pattern which is detected at a divided photodiode and amplified by means of a lock-in technique.

Apart from the optical method, also mechanical methods based on a small tuning fork of piezo-electrical material which is fastened on the microelectrode can be utilized for detection of the oscillation (James et al., J. Electrochem. Soc., 145 (1998), L64–L66). In this approach, the oscillation amplitude at the tip of the probe must be chosen to be so small that the electrochemical signal will not be substantially falsified. This precondition simultaneously constitutes the substantial limit for the use of ultramicroelectrodes and, thus, for an improved lateral resolution.

Moreover, each diminishing of the microelectrode involves significantly increased experimental expenditures (focussing of a laser beam on sub-$\mu$m electrode, searching for the resonance frequency etc.).

A further approach for an independent topographical recording has been described by Macpherson et al. (Anal. Chem., 72 (2000), 276–285). This is based on the production of microelectrodes whose geometry and properties are adapted to a cantilever. By a dynamic method, a platinum wire is symmetrically etched so that a tip forms. The wire is bent at an angle of 90°, and the vertical portion of the wire is pressed flat with the help of metal plates. By means of an electro-deposition lacquer, the microelectrode is electrically insulated. Due to its elasticity, the flattened portion serves for a distance control, based on the force interaction between sample and probe in the near field region.

With such tips and with the assistance of an AFM device, it has been possible to image sample surfaces, e.g. ultrafiltration membranes, in contact mode. With the approach described, electrodes having a variation width of the electroactive area in the $\mu$m and sub-$\mu$m-range could be produced, in which, simplified, a hemispheric geometry was assumed and the electro-active area was estimated with the assistance of cyclical voltametry.

However, the essential limits of this approach are to be seen both in the type of sample to be examined and in the little reproducible production of the electrochemical probes by the etching and insulating process, as well as in the poor topographical resolution due to the undefined tip geometry, as has been demonstrated by way of the quality of the recorded AFM images with decreasing tip size. The electrode illustrated by Macpherson et al. also gave rise to undesired contacts with the surface to be examined, for instance, the electrode got caught in pores of the surface. As a possible solution to this problem, Macpherson et al. proposed to use a non-contact version of this method in that at first, in a first step, the surface to be examined is topologically scanned with the cantilever, and then in a second, separate step the electrochemical examination is carried out at the known distance. However, this approach does not only involve considerably higher expenditures, but also has systematic errors, since hysteresis effects may occur in the positioning system used for the electrode, and already by this, an exact transmission of the topological information of a measurement process to a subsequent measurement process cannot be possible.

Publications based on a metallized cantilever in the electrochemical AFM experiment (cf. Macpherson et al., J. Am. Chem. Soc. 118 (1996), 6445–6452, Jones et al., J. Phys. Chem. B 104 (2000), 2351–2359) could not give a laterally resolved electrochemical information, on the one hand, since the metallized cantilever could only be manually insulated on the glass body, and a defined microelectrode having an insulated jacket could not be produced. The metallization served for the electrochemical surface modification (solution behavior of a (010) potassium-hexacyanoferrate-monocrystal), the topography of which was then determined in situ. On the other hand, with a metallized cantilever membranes were imaged on air which membranes were tensioned over a liquid-filled compartment such that the cantilever contacts the redox mediator-containing electrolyte solution merely at the pore openings. Due to the measurement arrangement, thus, the pores of the membrane could be electrochemically imaged despite a lack of insulation on the cantilever, since the humidity film covering the pore openings provides the lateral limiting (cf. Jones et al., Elechem. Commun. 1 (1999), 55–60).

Therefore, it was an object of the present invention to provide a device for simultaneously carrying out an electrochemical and a topographical near field microscopy.

Furthermore, methods for characterizing surfaces shall be provided in which both a topological and an electrochemical information on the surfaces to be examined are provided. Suitably, it should be possible to integrate the measurements methods and measurement electrodes to be newly provided into already existing measuring equipment without any considerable expenditures.

Further objects of the present invention comprise the provision of electrodes having a markedly improved measurement performance and measurement accuracy as compared to the prior art.

According to the invention, these objects can be achieved with a device for simultaneously carrying out an electrochemical and a topographical near field microscopy, which comprises a region for topographical near field measurement and a region for electrochemical near field measurement, the region for the topographical near field measurement extending, as usual, completely as far as to the immediate tip of the device (the probe for topographical near field measurement), with the electrode according to the invention being characterized in that the region for near field measurement starts at a defined distance from the immediate tip, the region for topographic near field measurement is covered by a conductive material except for the immediate tip, which conductive material is covered by an insulating material except for the region for the electrochemical near field measurement.

With the device according to the invention it has now become possible to keep constant the distance of the region for electrochemical near field measurement from the sample over a more or less conventional topographical near field measurement, and thus to carry out the electrochemical near field measurement without a systematic error caused by topological deviations of the surface.

What is essential for the device according to the invention which may be provided with integrated or combined electrodes is that the region for near field measurement does not extend as far as to the outermost tip of the device (probe) for topographic near field measurement, since this harbors the risk of a contact with the surface as well as of a negative influence on the near field measurement, but rather starts at a defined distance from the immediate tip.

The device according to the invention now allows for a simultaneous measurement of both, the topology, and also of the electrochemical properties in the near field of a surface, in that the topology is determined in a manner known per se via the immediate tip of the inventive device by means of topographical near field microscopy, while by way of this surface information, the inventive device simultaneously is adjusted relative to the sample such that it is located at a constant distance from the sample surface, wherein, also simultaneously, the electrochemical properties of the surface then are determined by the combined, preferably integrated, region for electrochemical near field measurement. Thus, the electrochemical or chemical information can be completely de-coupled from the topographical information, and by the precisely defined constant distance, a non-falsified electrochemical or chemical measurement signal can be quantitatively detected in correlation with the theoretically determined current values according to the solution of Fick's diffusion equation.

In the device according to the invention therefore also complex and error-prone devices for the shearing force-based height control (e.g. according to Ludwig et al.), and piezoelectric "testing devices" (such as, e.g., the "tuning fork" according to James et al.), respectively, are no longer required. Of course, the inventive device may, however, also be equipped with such elements, e.g. when specific experimental questions were to require it.

The distance which the region for near field measurement has from the the probe tip must be such that a contact of the sample by the tip will not result in any negative influences on the electrode. It is best if the dimension of the tip of the probe is adjusted such that both microscopy methods can develop as optimal as possible.

For the purposes of the present application, the term "electrode" is meant to comprise also all possible forms of ultramicroelectrode embodiments, including sensors or actuators.

By the integration of an ultramicroelectrode with a topological scanning near field probe, according to the invention the distance regulation of the integrated probe is adapted to any local, physical and chemical interaction between sample and inventive device in the near field. By this, a quantitative evaluation of the measured data is obtained according to the present invention.

The topological scanning near field microscopy (e.g. atomic force microscopy, AFM; scanning force microscopy, SFM) is characterized in that the topography and surface properties is measured with a resolution in the molecular to atomic range by surface forces between a sharp tip which, e.g., is fixed on a flexible lever arm (cantilever), and the sample, by deflection of the lever arm. General illustrations of various techniques applicable within the scope of the present invention for topographical and electrochemical near field microscopy (scanning probe microscopy) are shown in Bottomley (Anal. Chem. 70 (1998), 425R–475R) and in Wiesendanger (Scanning Probe Microscopy and Spectroscopy (Methods and Application) (Ed. R. Wiesendanger), Cambridge Press (1994)), which herewith are included as disclosure. Within the scope of the present invention, not only the topography of the substrate is mapped, but by the exact distance in the near field region of the electroactive area, also a height control in the electrochemical near field measurement is enabled.

This technology by which surfaces and atoms and molecules present thereon can be visualized with a resolution in the sub-nanometer range, is based on the work carried out by Binning et al. (Phys. Rev. Lett. 56 (1986), 930–933), also described in EP 0 027 517 A. This EP 0 027 517 A as well as those documents in which this EP-A has been cited shall herewith be included as disclosure for this technology. Various possible biological uses have been described, e.g. in Baselt et al. (Proc. IEEE85 (4) (1997), 672–679).

In contrast to the combinations of electrochemical and topographical scanning probe microscopy described in the prior art (Macpherson et al., Anal. Chem. 72 (2000), 276–285), according to the invention an even more precise device is provided which is even easier to produce, and allows for electrochemical measurements which can be carried out with fewer risks, in that the region for the electrochemical near field measurement does not extend as far as to the tip of the device, but ends at a defined distance behind the tip.

For the purposes of the present invention, as the "region for force measurement", or "region for electrochemical near field measurement", respectively, that part or region of the device is to be understood at which the respective interaction with the surface to be examined occurs, i.e. the effect to be measured is causally taken up into the measurement device as a signal. For the topographical near field measurement, as a rule this will be the immediate tip of a suitable AFM needle. The "region for electrochemical near field measurement" as a rule will be on the outer side of the electrochemical near field measurement device which faces the sample surface, e.g. on a metallic layer.

The defined distance to be provided according to the invention which the region for the electrochemical near field measurement has from the immediate probe tip which is used for topographic near field measurement, may vary within wide ranges depending on the respective resolution that is to be attained. According to the invention, defined distances of the region for electrochemical near field measurement from the immediate probe tip ranging from 2.7 mm to 10 nm, preferably 1 mm to 50 nm, in particular 0.5 mm to 100 nm, have proven particularly suitable.

Furthermore, according to the invention by "immediate tip" that part of the probe or device tip is understood which is located at the outermost end of this tip and may, e.g., be only a few atoms in size. Hence follows that according to the invention the region for electrochemical near field measurement, as a rule, will lie on the tip portion of, e.g., a cantilever, yet not on the immediate tip an which the topographical near field measurement is carried out. If the near field interaction for topographic imaging is based on a contact-free scanning near field technique, the region for electrochemical near field measurement may however, as an exception, extend as far as to the tip.

Furthermore, according to the invention also the region by which information on the topology of the surface is obtained, and the region for electrochemical near field measurement are rigidly positioned relative to each other, e.g. in contrast to shearing-force-based height controls and other methods in which vibration producing means (piezoelectric elements) are used to obtain such information regarding the surface.

With the device according to the invention, not only contacting of the sensitive electrode by the surface and the measurement error involved therewith and mechanical risks for the combined or integrated electrode are avoided, but also a subsequent examination of the surface (first the topology, then the electrochemical information), as it has been suggested as a solution to the problem by Macpherson et al., can be avoided.

Therefore, what is essential is that the region for electrochemical near field microscopy is created by covering the device for topographical near field measurement ("tip", "cantilever") by a conductive material. Such covering may be complete ("envelope"), yet it is also possible to cover merely certain regions of the device for topographical near field measurement (e.g. in the form of conductive tracks along the longitudinal axis of the cantilever) with conductive material.

In case that the device for topographical near field measurement itself is conductive (e.g. in the scanning tunneling microscope tip; "scanning tunneling microscopy" (STM); or in scanning near field optical microscopy (SNOM) tips)), this conductive device itself must, of course at-first be insulated in the device according to the invention, and on this insulating layer, the conductive material for the electrochemical near field measurement must be present. In this instance, the insulated form of the device for topographical near field measurement is (at least partially) covered with the conductive material so as to provide the device for electrochemical near field measurement which, in turn, then must also be insulated (with the exception of the measurement region).

This insulation of the device according to the invention is essential since the electrochemical near field measurement always must be performed in a liquid medium (electrolyte; liquid, conductive phase), and accordingly, those parts of the device for the electrochemical near field measurement which do not serve for the immediate measurement ("measurement area") must be protected against the liquid medium present during the measurement, which medium, as a rule, covers the surface to be measured, so as to avoid any undesired influences on this measurement.

Preferably, the device according to the invention consists of a force microscope tip which, with the exception of the immediate tip, is enveloped by conductive material, which material, except for the region for electrochemical near field measurement, is covered by an insulating material.

One example of such a layer assembly is illustrated in FIG. 10, wherein (1) indicates the region for topographical near field measurement, (2) indicates the region for electrochemical near field measurement, and (3) indicates the insulating material. (4) represents the connection area which is electrically conductively connected with the region for electrochemical near field measurement.

The thickness of the region for the electrochemical near field measurement, or of the conductive material, respectively, will also depend on the respective resolution to be achieved, and the material used, respectively. Preferably, these thicknesses will range from 10 to 2000 nm, preferably from 100 to 800 nm, in particular from 150 to 500 nm.

Preferably, the region for the electrochemical near field measurement consists of a metallic element, in particular a transition metal, the use of gold, silver, platinum, palladium, tungsten, antimony, rhodium, iridium, mercury alloys, a platinum-iridium-alloy, a platinum-rhodium-alloy, carbon, glassy carbon, high-order pyrolytic graphite (HOPG) being particularly preferred. Furthermore, also other materials, such as polysilicon, in particular doped polysilicon, metal nitrides, in particular TiN or TaN, or silicides, in particular tungsten silicide or tantalum silicide, may be used.

According to the invention, the inventive device may also be equipped with further layers or with different layer sequences, respectively, and thus be provided with a modified electrode which is designed as a microbiosensor, such as, e.g., an enzyme electrode, a pH-sensitive ultramicroelectrode, a potentiometric or amperometric ultramicroelectrode, an ion-sensitive ultramicroelectrode, an ion-selective ultramicroelectrode, a polymer-modified ultramicroelectrode, a biomimetic ultramicroelectrode. The number and arrangement of the various regions for the electrochemical near field measurement in such a multi-electrode and multi-sensor configuration, accordingly, can be increased deliberately, by varying this layer sequence and the number of layers so as to enable a multi-parameter measurement, such as, e.g., simultaneous, electrochemical, topographical and pH-mapping.

According to a preferred embodiment, the inventive device therefore is designed with electrodes configured as multi-electrodes and/or multi-sensors, wherein preferably measurement probes designed for different measurement methods are provided.

Furthermore, also several tips may be provided for topographical near field measurement, or several inventive combination devices may be provided for topographical and electrochemical near field measurement in one and the same device.

Furthermore, the possibilities of using the device according to the invention exceed those known for the electrochemical scanning microscopy (cf., e.g., U.S. Pat. No. 5,202,004 as well as U.S. Pat. No. 5,382,336, whose disclosure herewith is incorporated herein), in that now it has become possible to examine any desired surface systems which are covered by an electroactive medium.

Preferred applications of the devices according to the invention are the examination of biochemical, biological or biomimetic coats, of neurophysiological problems, such as cell communication, concentration determinations in extracellular matrices, membrane characterizations and transfer phenomena, electron, ion and molecule transfers at phase interfaces, the study of homogeneous and heterogeneous electron transfer reactions, corrosion phenomena, such as, e.g., corrosion of metal and semiconductor surfaces, the formation of corrosion/defect sites or the like material-scientific studies, with the examination of biological-medical questions as well as questions in connection with semiconductors being considered as particularly preferred.

The present invention can also be used for surface modification or surface structuring by etching (removal of material) and/or deposition (application of material).

On the one hand, depositing as well as etching processes may be carried out in a double-electrode arrangement, with the microelectrode acting as the counter-electrode and the substrate acting as the working electrode. Modifications can be carried out not only in electrolyte solutions, but also in solid ionic conductors. By applying a potential between counter-electrode and working electrode, reduction processes and oxidation processes, respectively, can be induced on the interface substrate electrode/electrolyte, and ionic conductor, respectively, so that deposits or etchings, respectively, in the size of the microelectrode can be produced by the local electric field. On the other hand, in a four-electrode arrangement, a suitable mediator can be reacted at the microelectrode which diffuses to the substrate (conductive or non-conductive), and there induces a depositing process or an etching process, respectively, by oxidation or reduction, respectively. Depositing and etching, respectively, may be performed on metals, semimetals and alloys, moreover also polymers can be produced which can be prepared by electrochemical polymerisation (cf. Mandler et al., Isr. J. Chem. 36 (1996), 73–80).

Especially by the preferred layered assembly, the dimensioning of the region for the electrochemical near field measurement can reproducibly be diminished. Compared to the methods described in the literature which depart from the form of a wire, the provision of thin layers is technically much easier and more reproducible than in case of the wire form.

The tip of the inventive device may, if necessary, be particularly adapted to the topological examination, as is known per se for force microscopy, and designed as a sensor or actuator, and have special coats, in particular if, e.g., special biological questions have to be addressed.

According to other preferred embodiments, the device according to the invention can also be designed such that a topographical near field tip, e.g. an AFM tip, carries a conductive layer insulated relative to the medium merely along one side, e.g. Furthermore, also the region for electrochemical near field measurement may also be laterally provided, or generally other geometries may be chosen for the electrode. The topographical scanning measurement in contact mode just as in the tapping mode requires a sharp tip since the obtainable resolution depends on the radius of curvature. The integrated ultramicroelectrode, however, may preferably have the shape of a ring, a frame, a disc or have a conical or cylindrical shape (for these geometries there already exist theoretical descriptions of the current signal, except for the frame shape).

In a further aspect, the present invention also relates to a method for the ultramicroscopic examination of surfaces, which is characterized in that by means known per se, an inventive device is brought into the vicinity of the surface to be examined, so that both the distance to the surface may be measured by a topographical near field technique and also an electrochemical near field measurement of the surface can be carried out, and the surface is examined by moving the device over the surface, with the information obtained by the topographical near field technique being directly used to keep the inventive device at approximately the same distance from the surface so that the electrochemical near field measurement can be carried out without being impaired by topological fluctuations.

With this, for the first time a simultaneous electrochemical near field microscopy and a topographical near field measurement has become possible, which is not impaired by any systematic errors in the correlation of the two microscopic techniques.

Finally, the present invention also relates to a near field microscope for the ultramicroscopic examination of surfaces, comprising a device according to the invention, an analysis unit in which the measurements made at the device are recorded and processed, means for transferring the electrochemical near field measurement from the device to the analysis unit, means for transferring the topographical near field measurement from the tip of the device to the analysis unit, and manipulation elements for the inventive device which are controllable by the analysis unit.

This inventive near field microscope can be adapted by the person skilled in the art without difficulty on the basis of known device and measurement elements for the topographical near field measurement, on the one hand, and for the electrochemical near field measurement, on the other hand, with the help of the present teaching.

Surprisingly, it has been shown that the inventive device can easily be integrated, e.g., in AFM microscopes already on the market, and the information regarding the electrochemical near field measurement as well as for carrying out the equidistant near field measurement itself can be carried out by mere handicraft steps. As a rule, the AFM apparatus already on the market, such as, e.g., the Digital Instrument Nanoscope III, in addition to the channels provided for the intended data recordal also have one or further analogous input channel(s) on the data registering device, which allow for an additional reading-in of measurement data, e.g. the electrochemical measurement data, and the correlation and representation with the simultaneously registered topographical data (cf. FIG. 4).

At the same time, the present invention also provides a simple method for producing the device according to the invention, in which a topographic near field microscopy probe is covered with a conductive material, and the conductive material is covered by an insulating layer, and the conductive material on the insulating layer is removed in the region of the immediate tip of the probe. With the present method, not only a suitable ultramicroelectrode which allows for electrochemical examinations of surfaces with a simultaneous determination of the surface topology can be produced, but according to the invention the well-reproducible production of these electrodes is made possible with an amazingly simple method. The method according to the invention can also be easily included in already existing manufacturing processes, since, e.g., conventional force microscopy probes can be used as the starting material. By the method according to the invention it is ensured that the electrochemical near field measurement region of the device, which region is defined by the conductive material which, after removal of the insulating layer, is capable of accepting the signals received from the sample surface, does not extend as far as to the outermost tip of the device, but starts at a defined distance from the immediate tip of the device (on which the interaction with the surfaces, measured for the topological imaging, occurs). In this manner, not only the risk of a contact of the electrochemical near field measurement device with the surface is prevented, but also a negative influence of the topological near field measurement is avoided.

What is essential to the method according to the invention is that, starting from a probe suitable for topological near field measurement, by applying and insulating a conductive material, the electrochemical near field measurement can be combined with the topological near field measurement in a simple manner. By removing conductive material and insulating layer in the region of the immediate tip of the probe suitable for topographic near field measurement, not only the functioning ability of the tip required for the topographical near field measurement is restored again, but also a region is created with which the conductive material is made accessible again for measuring surface effects in the electrochemical near field. The insulating layer applied over the conductive material has the effect that the signals will only enter via the region which has deliberately been uncovered.

The manner in which the topological near field probe is covered with the conductive material is not critical. In general, for reasons of process technology, it will be preferred for the topological near field probe to be enveloped with the conductive material. It is, however, also possible to provide, e.g., merely one side of the probe with the conductive material. What is essential is only that the conductive layer is supplied from the region in which the electrochemical near field interaction with the surface is to be measured, to a suitable site of contact in another region of the inventive device, from which site the measurement signal can be taken.

The preferred conductive materials are either metals or they contain a metallic component, in particular a transition metal, the use of gold, silver, platinum, palladium, tungsten, and antimony. Furthermore, also materials, such as polysilicon, titan nitride, rhodium, iridium, mercury alloys, a platinum-iridium-alloy, a platinum-rhodium-alloy, carbon, glassy carbon, high-order pyrolytic graphite (HOPG) may be considered as preferred materials. Furthermore, also other materials, such as polysilicon, in particular doped polysilicon, metal nitrides, in particular TiN or TaN, or silicides may be used.

The manner in which the topographical near field microscope probe is covered with the conductive material is not critical and will depend on the respective material to be applied. Particularly suitable methods comprise ion sputtering, electron sputtering, chemical vapor deposition (CVD), electroless plating, electroplating and so on, in individual cases, however, also liquid phase deposition processes and spincoating methods are conceivable.

The covering of the layer of conductive material with the insulating layer preferably is effected by deposition from the gas phase, by a chemical vapor deposition process, in particular, however, also by a plasma-supported CVD process, ion sputtering, electron sputtering, electroless plating, electroplating and application of insulating polymer layers, yet in individual cases also liquid phase deposition processes and spincoating methods are conceivable. With the insulation it must be ensured that the conductive material is completely covered so that the conductive material (except for the measurement region bared later on) does not have any contact to the electroactive medium.

The uncovering of a certain region of the conductive layer is effected by the intentional removal of the insulating layer and the layer of conductive material. The removal of the conductive material and/or the removal of the insulating layer preferably are effected by a focussed ion beam, optionally a neutral particle beam, by an etching process, by laser or by focussed electromagnetic waves, removal by focussed ion beam being particularly preferred (cf. e.g. Matsui et al., Nanotechnology 7 (1996), 247–258).

The dimensioning of the layers (with which essentially the region is defined with which the electrochemical near field defects are measured) will depend on the respective field of use and/or the resolution ability of the inventive device, and accordingly preferably the conductive material will be applied in a thickness of from 10 to 2000 nm, preferably from 100 to 800 nm, in particular from 150 to 500 nm. Yet also a monoatomic or monomolecular conductive layer is conceivable.

Preferably, the insulating layer will be applied in a thickness of from 50 to 5000 nm, preferably from 100 to 2000 nm, in particular from 500 to 1500 nm, and for the examination of chemically inert or non-conductive substrates, respectively, it must be correlated with the electroactive area of the electrode, since the diffusion blocking in such samples clearly depends on the area of the insulating layer (cf. Mirkin et al., J. Electroanal. Chem. 328 (1992), 47–62).

The numerical solution of the differential equations for insulators have been determined with a ratio of radii of electroactive area/insulating jacket (RG) of 10. (Cf. Kwak et al., Anal. Chem. 61 (1989), 1221–1227). However, the layer thickness must ensure a sufficient insulation of the electroactive area and should not fall below an RG of 10, since the experimental values then will be significantly higher than the data obtained by simulations. Here, too, however, also monoatomic or monomolecular layers are conceivable.

The region in which the conductive material and the insulating layer are removed will also depend on the planned field of application of the device according to the invention and its measurement characteristics, respectively, and will also depend on the respective method of removing these layers. Preferably, a region from the immediate tip as far as to a distance from the immediate tip of from 10 to 2000 nm, preferably from 50 to 1000 nm, in particular from 100 to 500 nm is removed, wherein in each individual case the particular geometry of the probe suitable for topographical near field measurement, which geometry forms the basis from which it is started out with, must be taken into consideration.

Preferably, it is already provided in the inventive production method itself that suitable connecting devices are provided at the inventive device for recording the measurement signals.

The invention will be explained in more detail by way of the following exemplary embodiments as-well as drawing figures to which, however, it is not restricted.

Therein,

Figure 4:
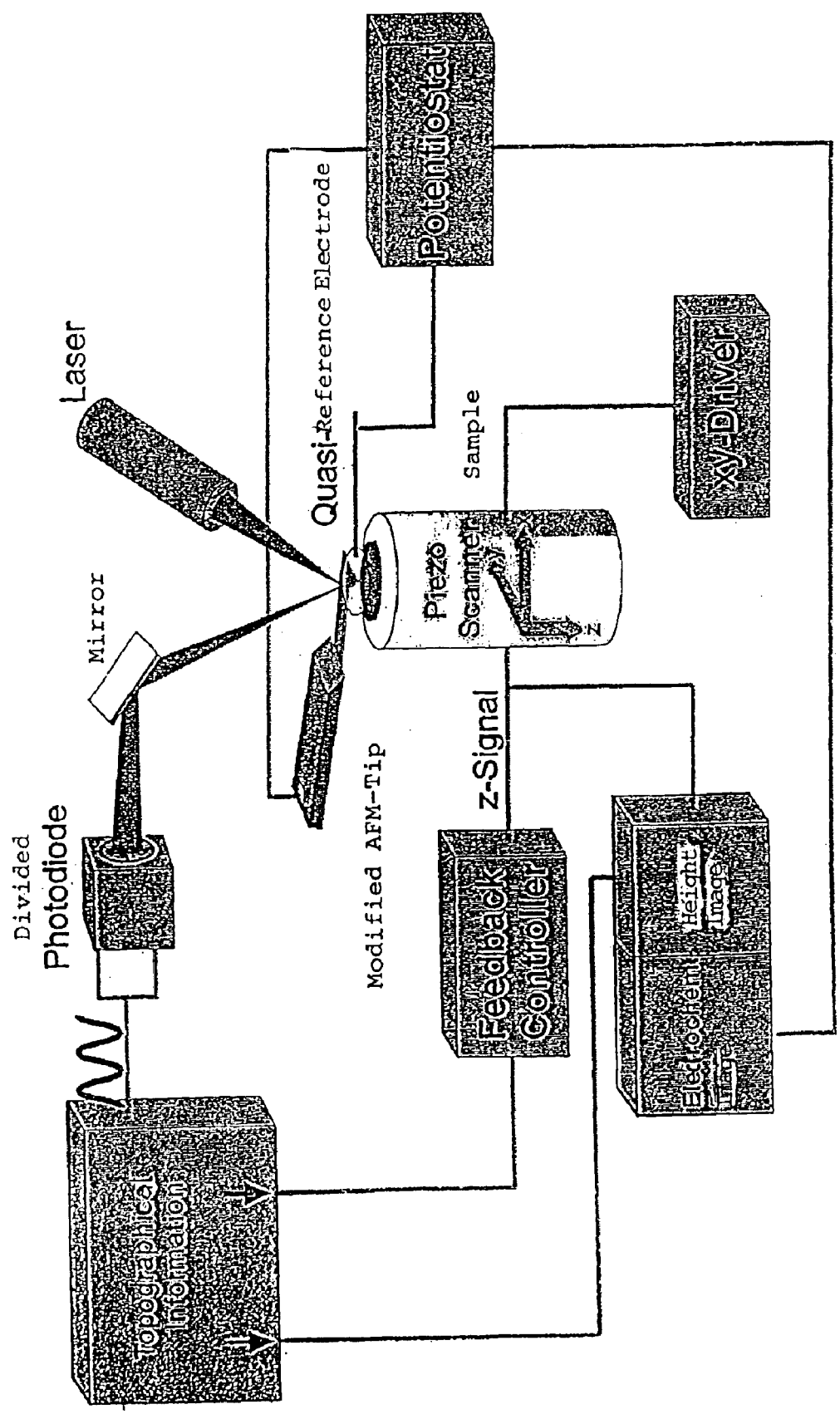
Figure 5:
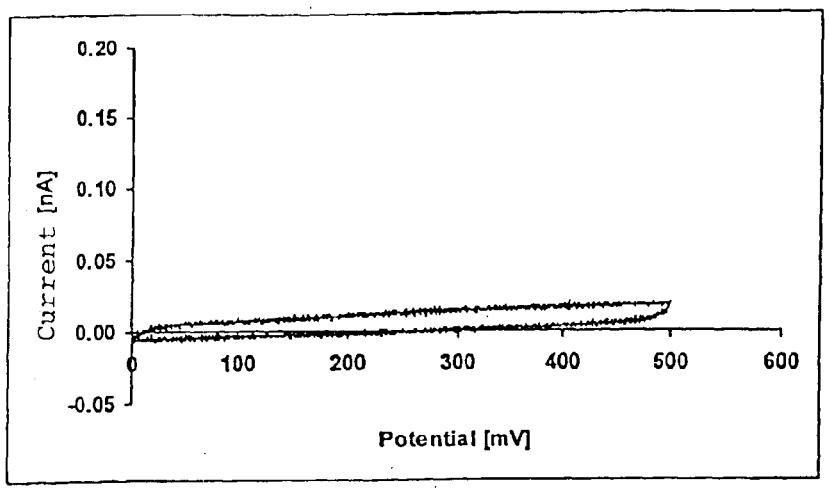

(b) the schematic illustration of the distance control via the optic detection method and recycling of the electroactive substance in the near field range by a conductive or chemically active sample surface;

FIG. 4 shows a schematic illustration of the measurement assembly if the inventive near field probe is based on an AFM cantilever;

FIG. 5 shows a cyclical voltammogram of an insulated near field probe 200 nm gold, 800 nm insulation, taken up in 5 mM $K_4[Fe(CN)_6]/0.1$ M KCl; advance speed 100 mV/s.

Figure 6:
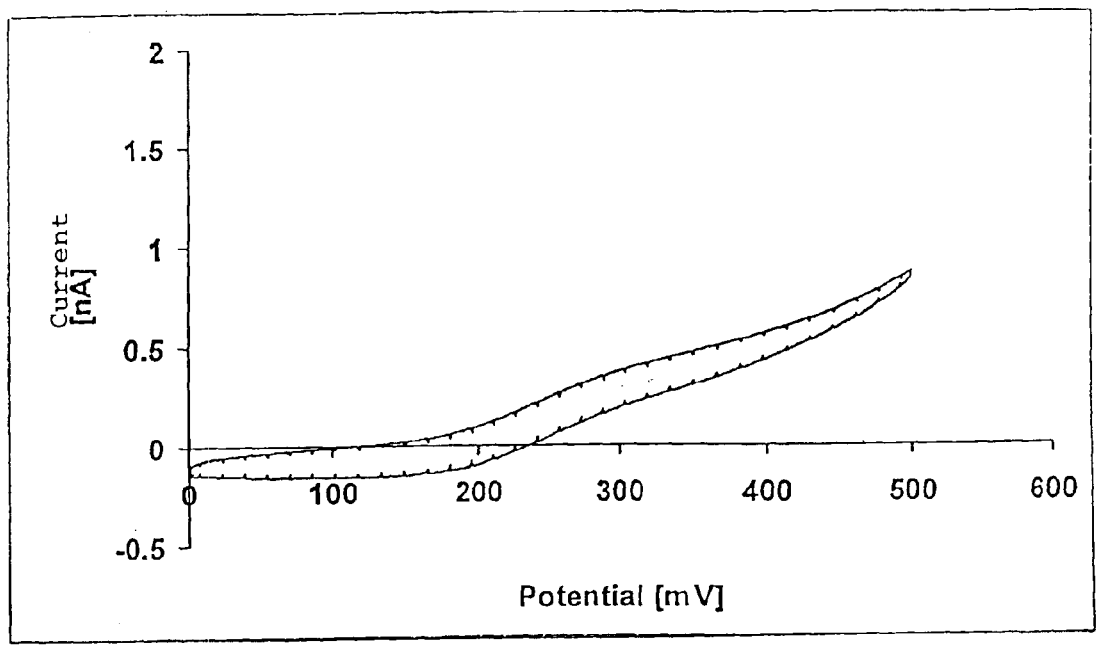
Figure 7:
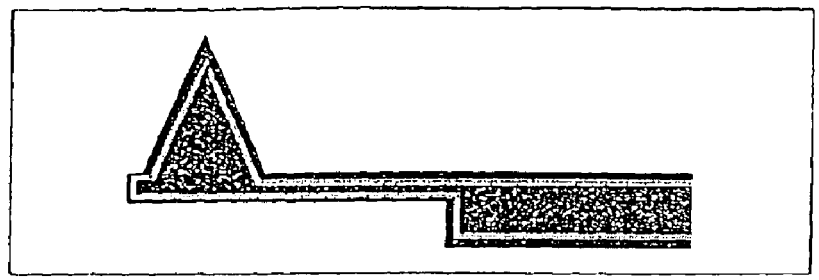
Figure 7:
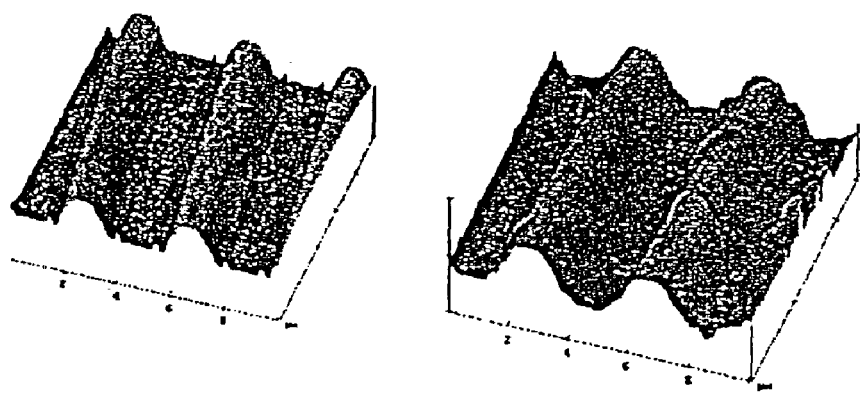
Figure 8:
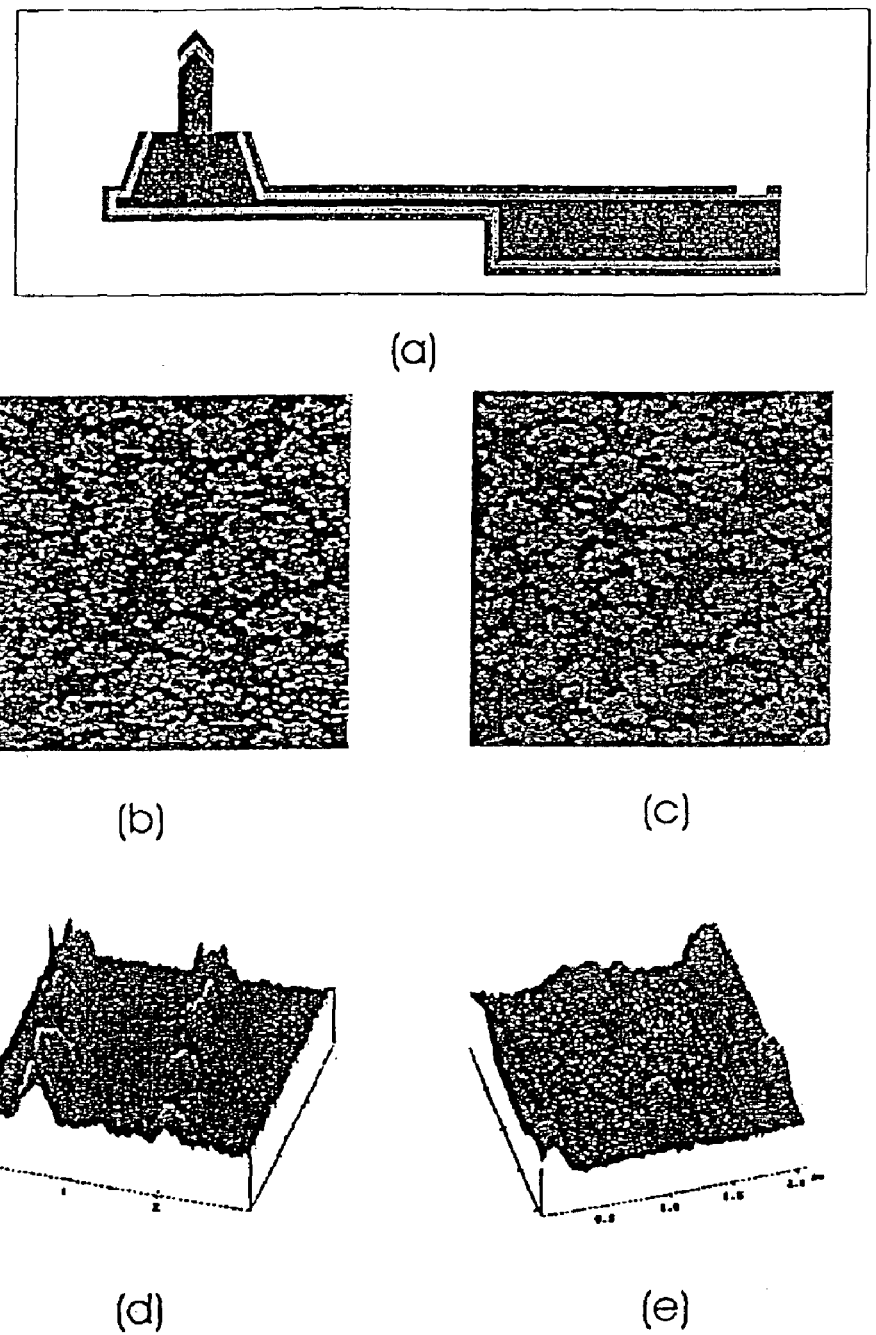

FIG. 6 shows a cyclical voltammogram of an integrated electrochemical near field probe 100 nm gold, 800 nm insulation, taken up in 5 mM $K_4[Fe(CN)_6]/0.1$ M KCl; advance speed: 100 mV/s;

FIG. 7 shows (a) a schematic illustration of an exemplary AFM cantilever after application of an electroactive layer and an insulating layer;

(b) the AFM image of a gold-GaAS-grid with a periodicity of 3.4 $\mu$m with a commercial $Si_3N_4$ cantilever in contact mode;

(c) the AFM image of the gold-GaAS grid with a periodicity of 3.4 $\mu$m with the inventive metal-coated (200 nm gold) and insulated (800 nm nitride) AFM cantilever in contact mode;

FIG. 8 shows (a) a schematic illustration of the exemplary AFM cantilever after the first two milling steps;

(b) the AFM image of a p-doped silicon surface after deposition of octadodecyl siloxane islands, imaged with a commercial $Si_3N_4$ cantilever in the contact mode (imaging grid 10×10 $\mu$m) island size ~1–2 $\mu$m, height ~2.6 nm.

(c) the AFM image of the octadecyl siloxane islands in the contact mode (image grid 10×10 $\mu$m) with the inventive modified probe (200 nm gold, 800 nm insulation layer, radius of curvature ~300 nm, height ~2 $\mu$m (production step FIG. 13a)).

(d) an image of 300 nm gold dots on a GaAS substrate with a commercial $Si_3N_4$ cantilever, in the contact mode.

Figure 9:
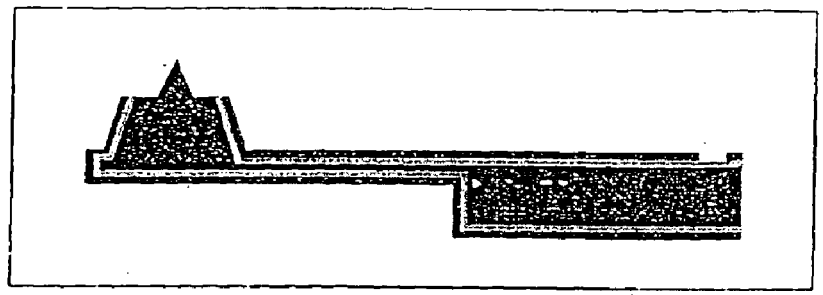
Figure 9:
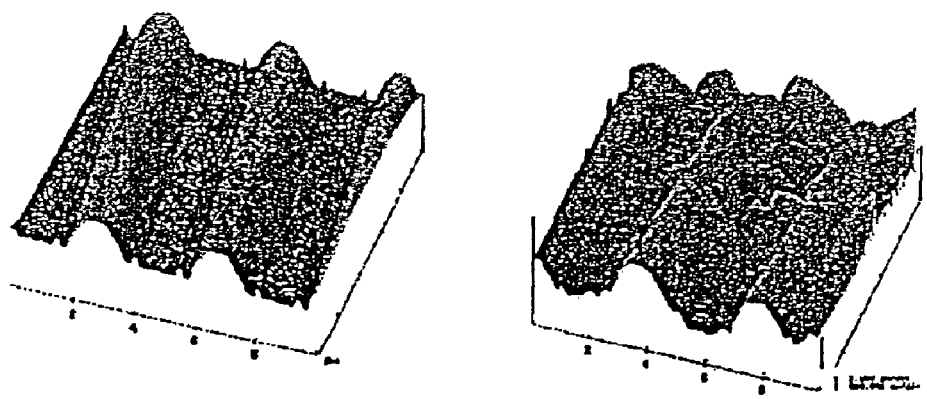

(e) an image of 300 nm gold dots on a GaAs substrate in the contact mode with the inventive modified probe (200 nm gold, 800 nm insulation layer, radius of curvature ~300 nm, height 2 $\mu$m; and FIG. 9 shows (a) a schematic illustration of an inventive scan near field probe with an integrated ultramicroelectrode based on an AFM cantilever.

(b) the AFM image of a gold-gaAS grid with a periodicity of 3.4 $\mu$m with a commercial $Si_3N_4$ cantilever in the contact mode on air. (c) the AFM image of the gold-GaAS grid with a periodicity of 3.4 $\mu$m in the contact mode with an inventive scan near field probe with integrated ultramicroelectrode (tip height ~1 $\mu$m).

Figure 10:
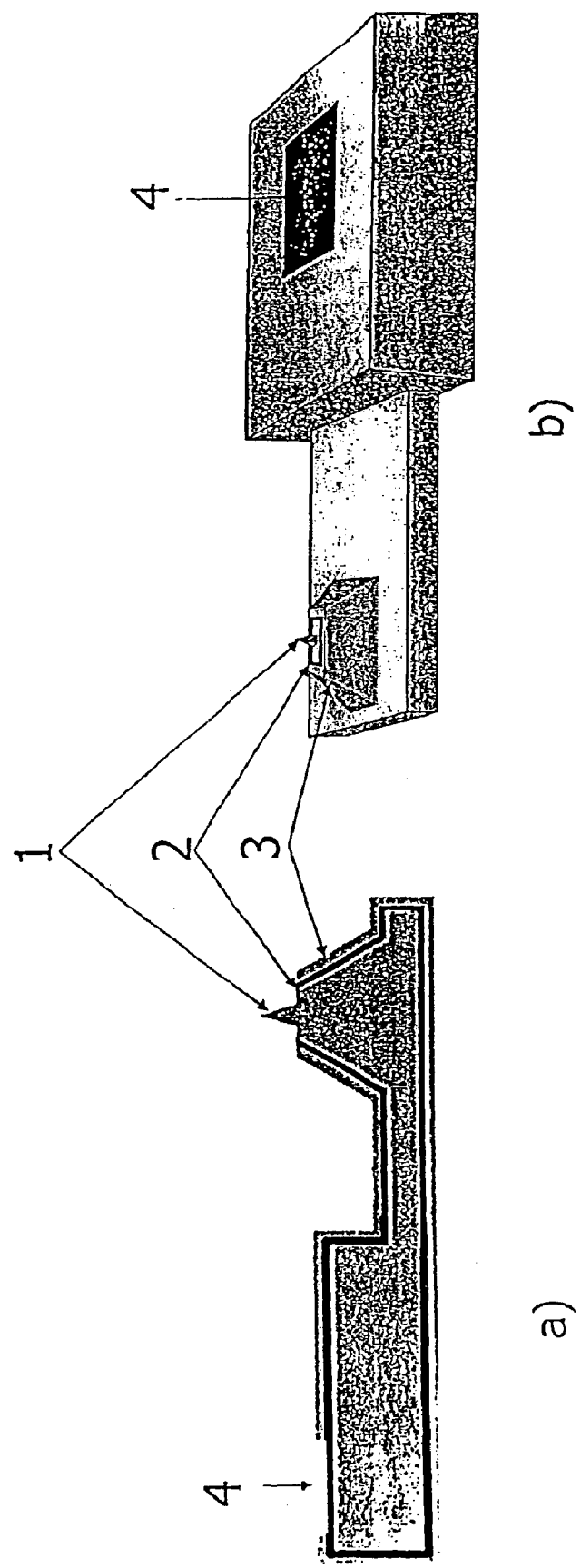
Figure 11:
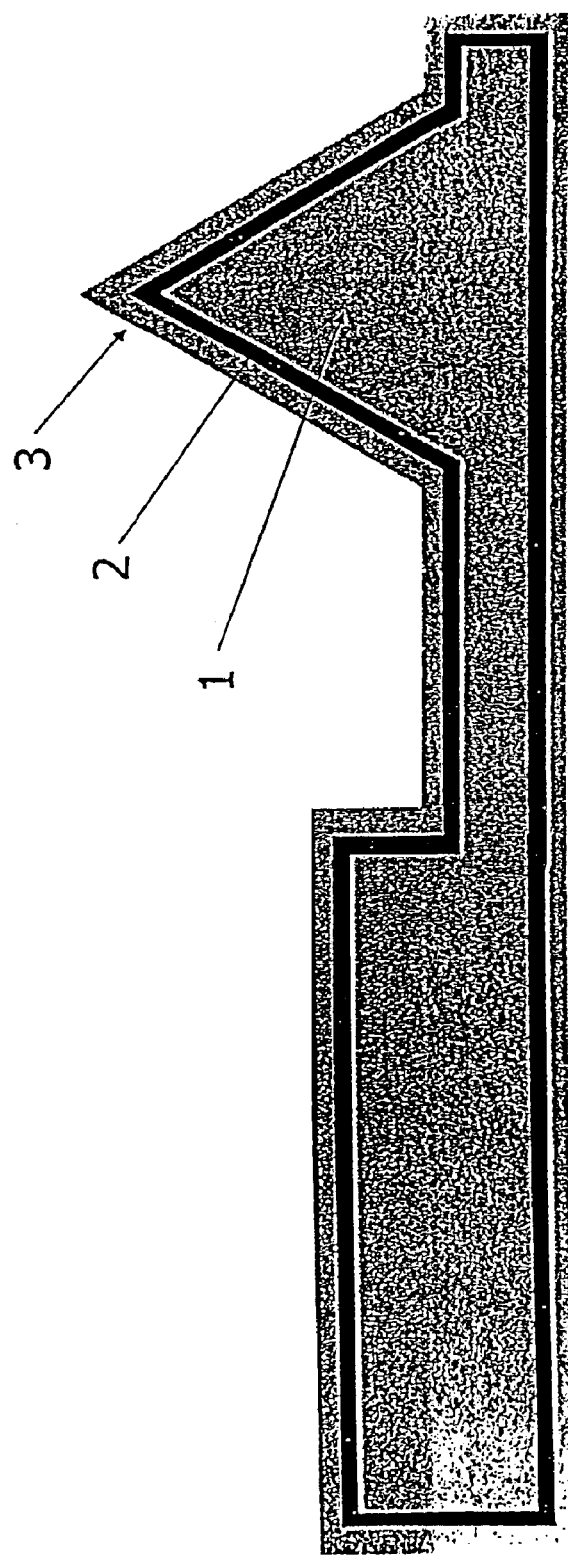
Figure 12:
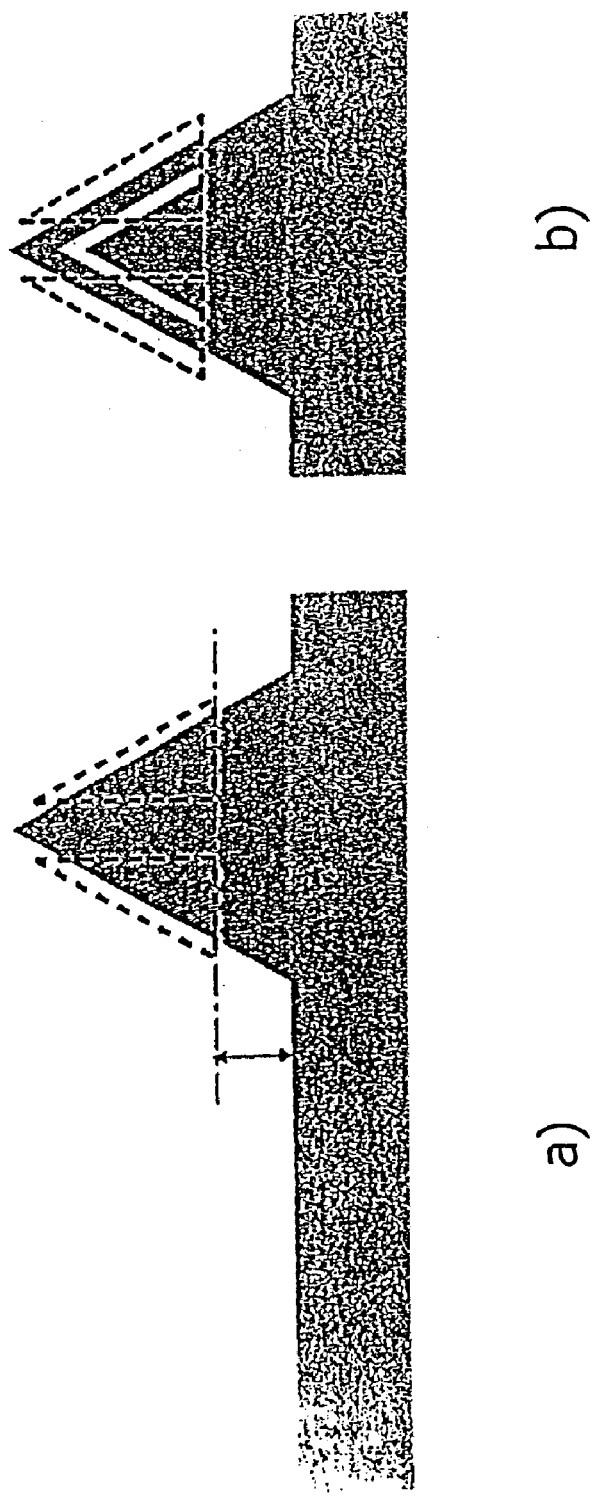
Figure 13:
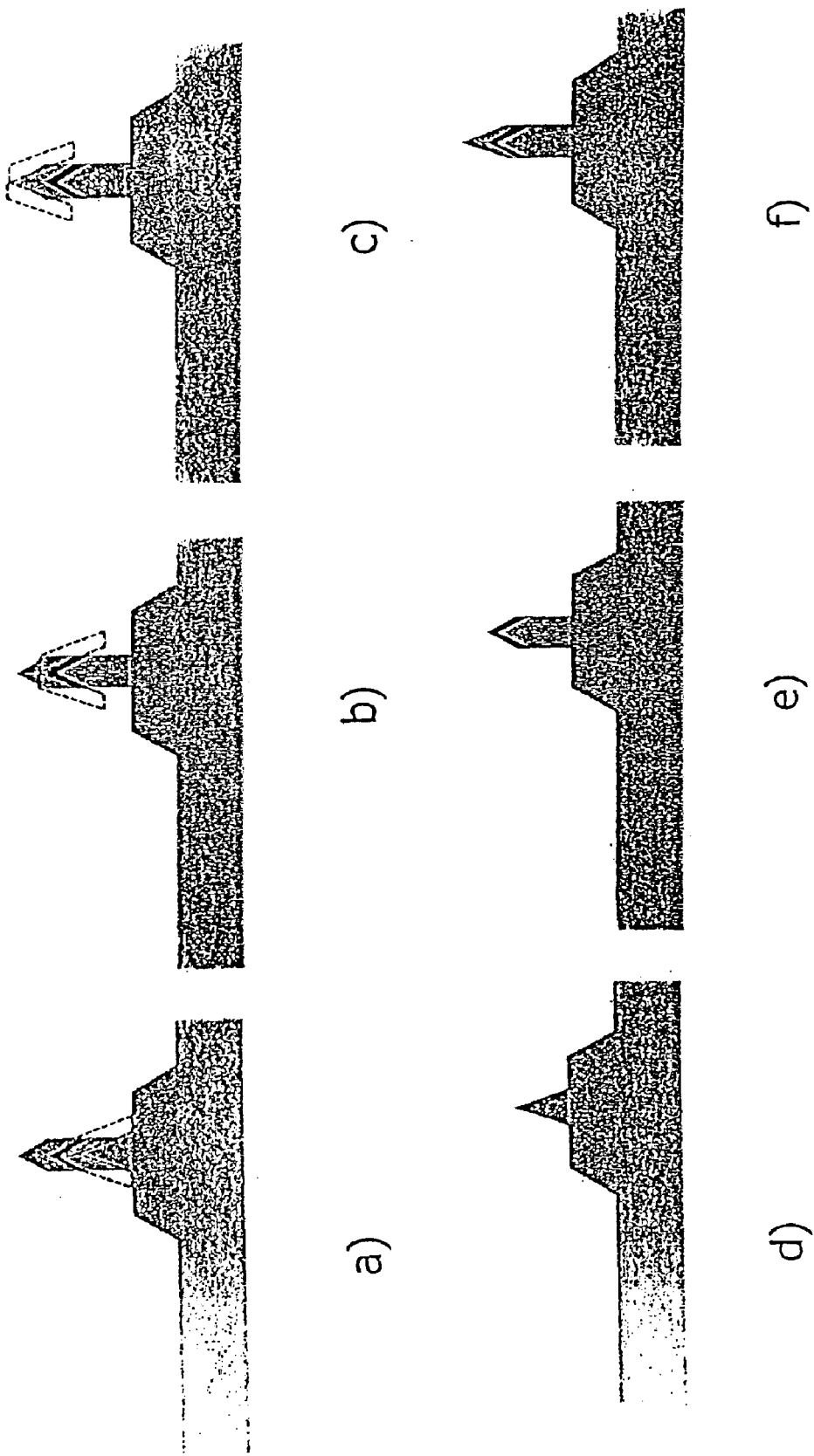
Figure 14:
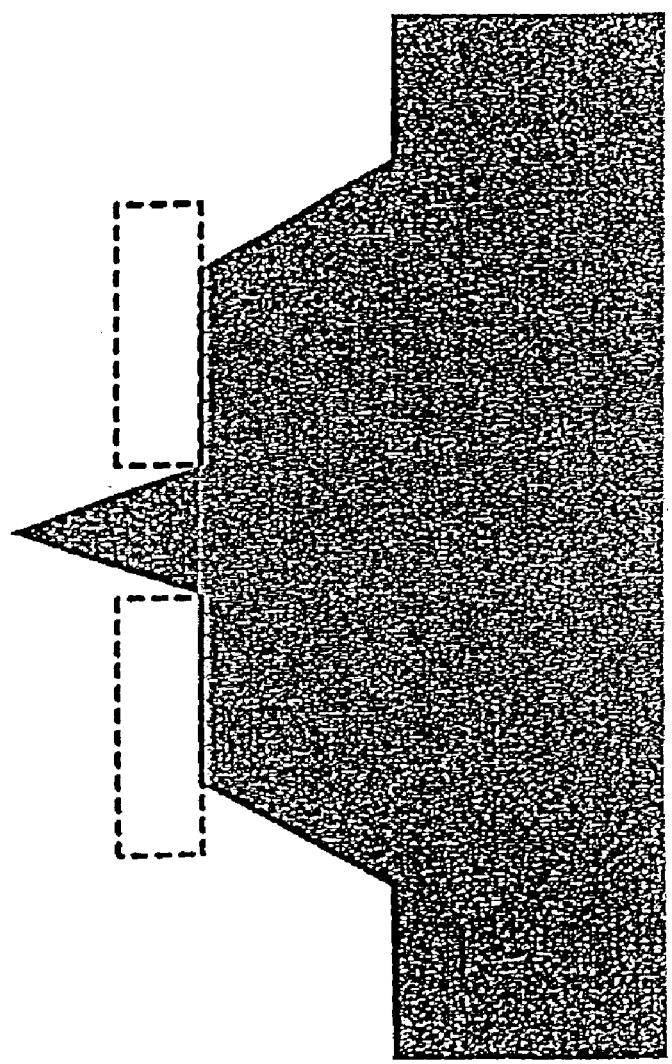
Figure 15:
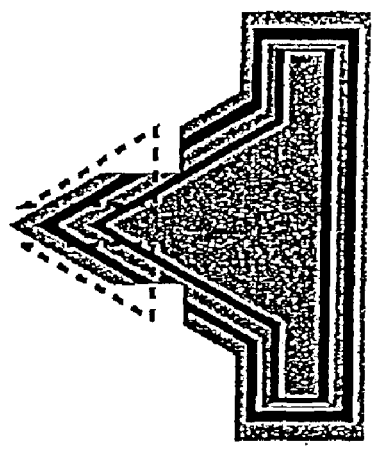
Figure 15:
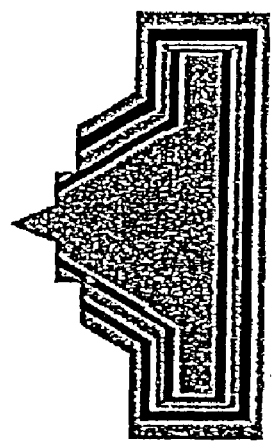
Figure 15:
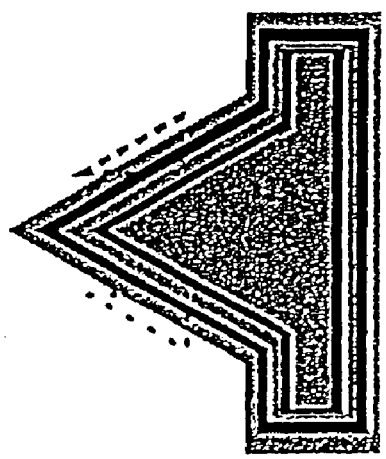
Figure 15:
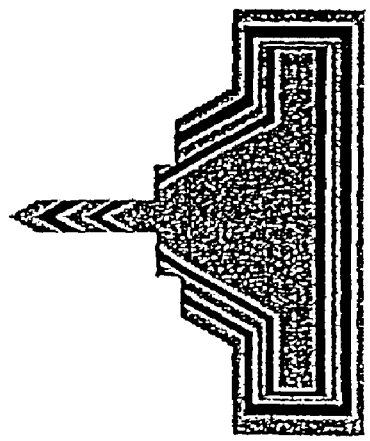
Figure 16:
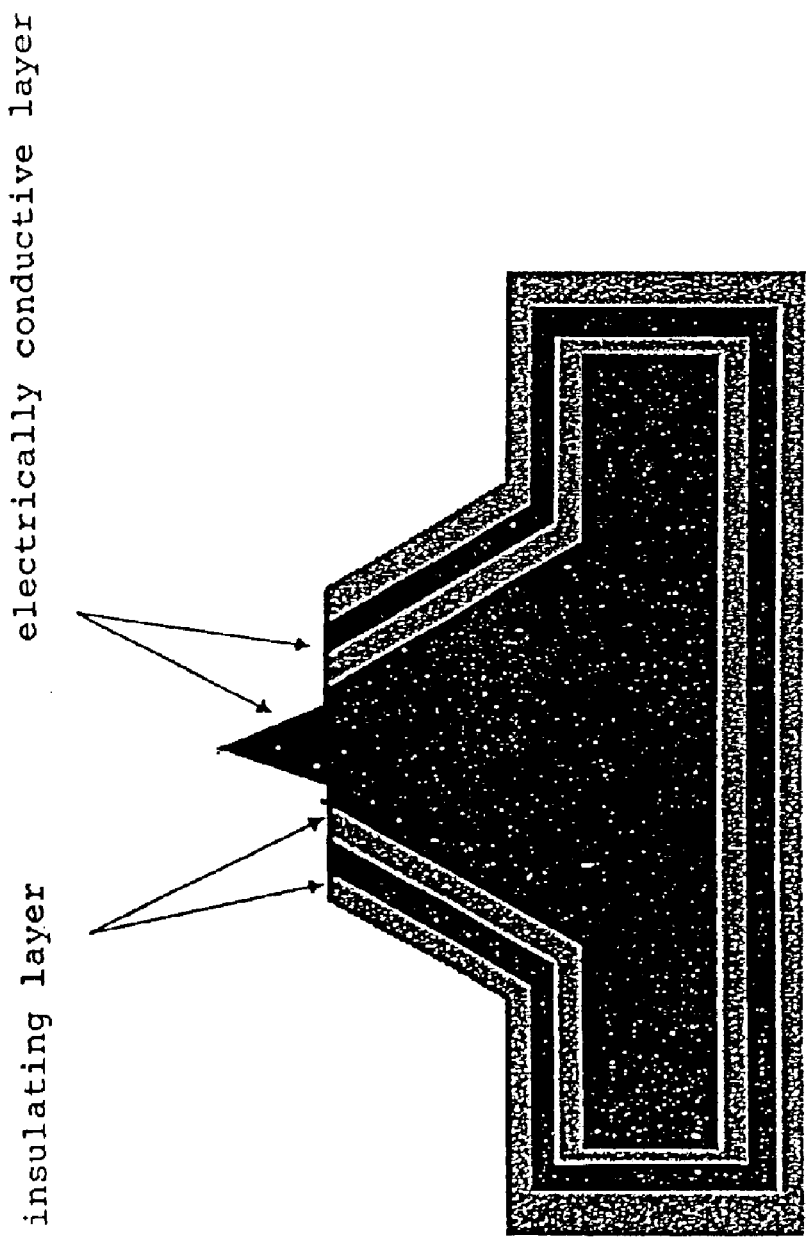
Figure 17:
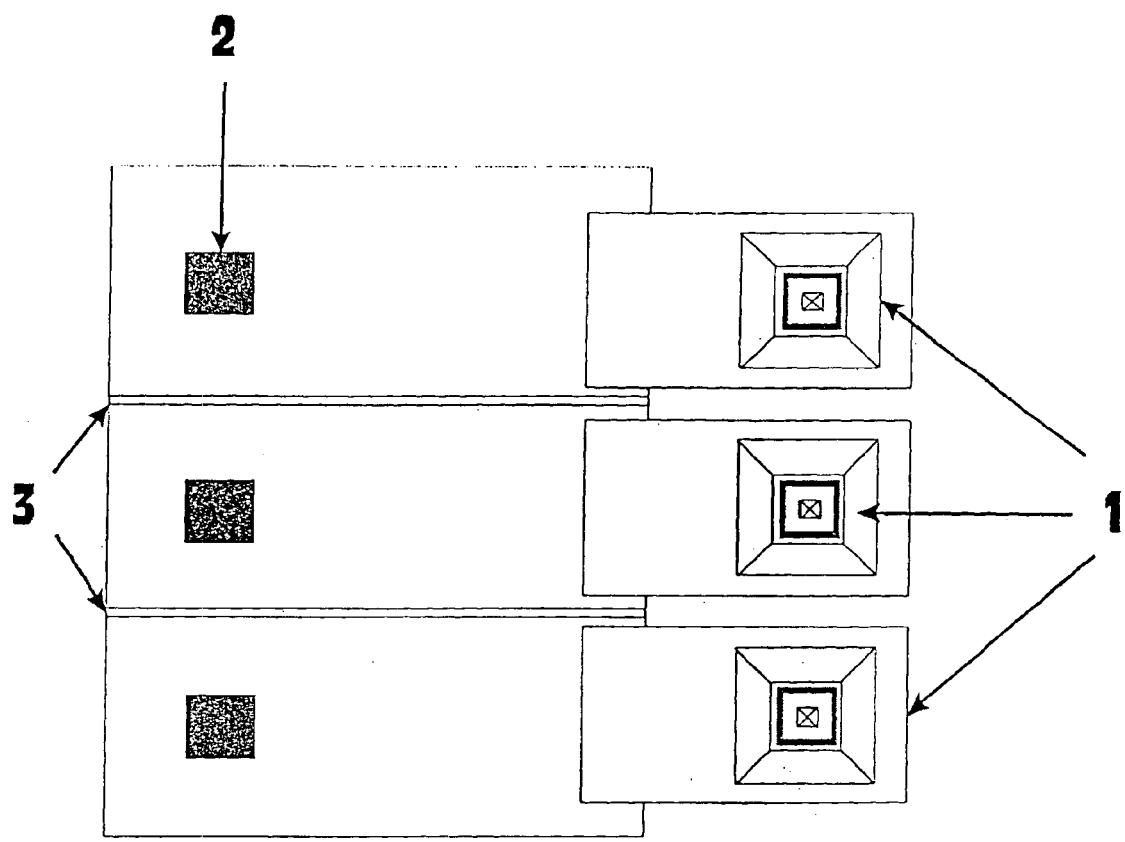
Figure 18:
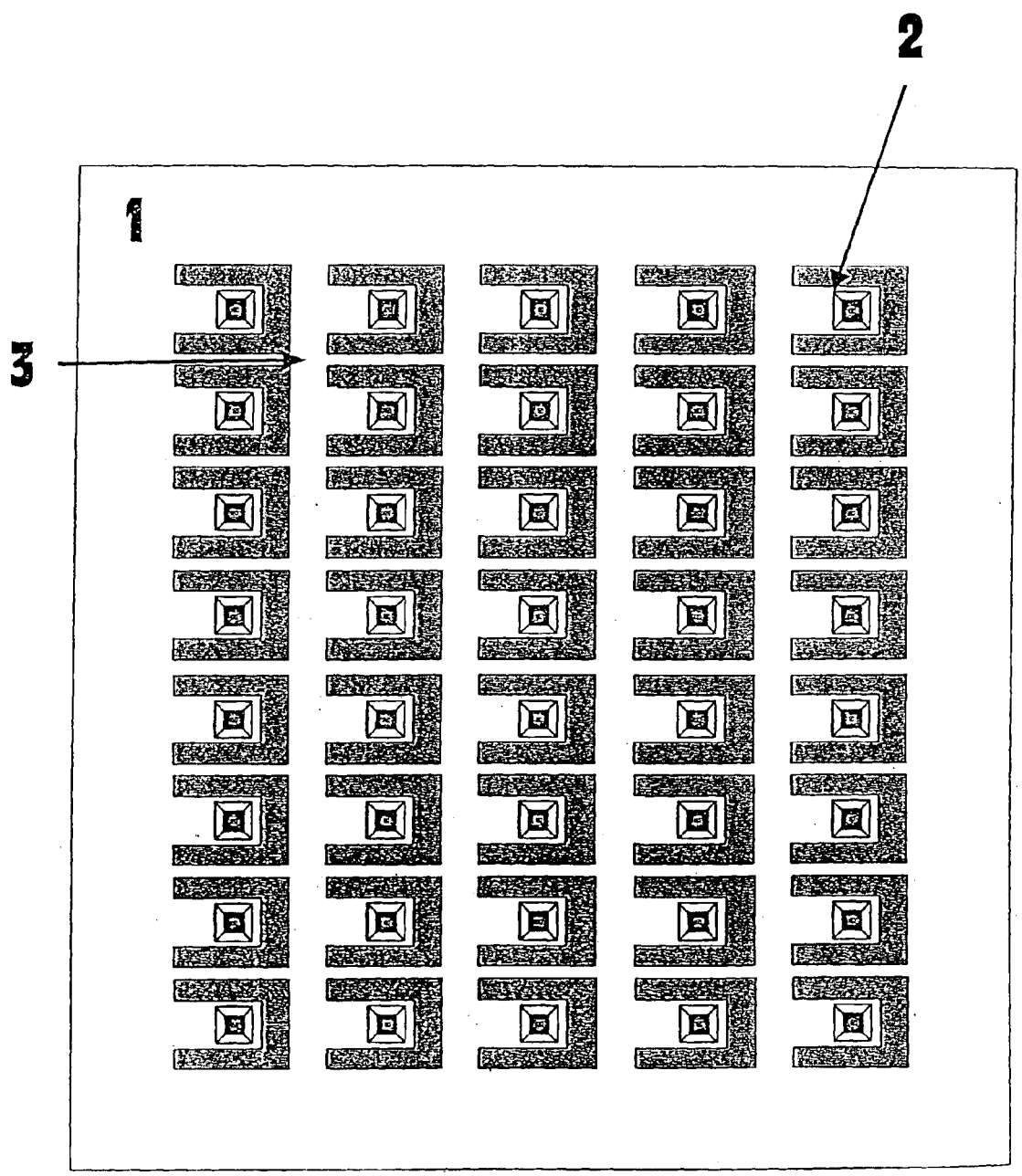
Figure 19:
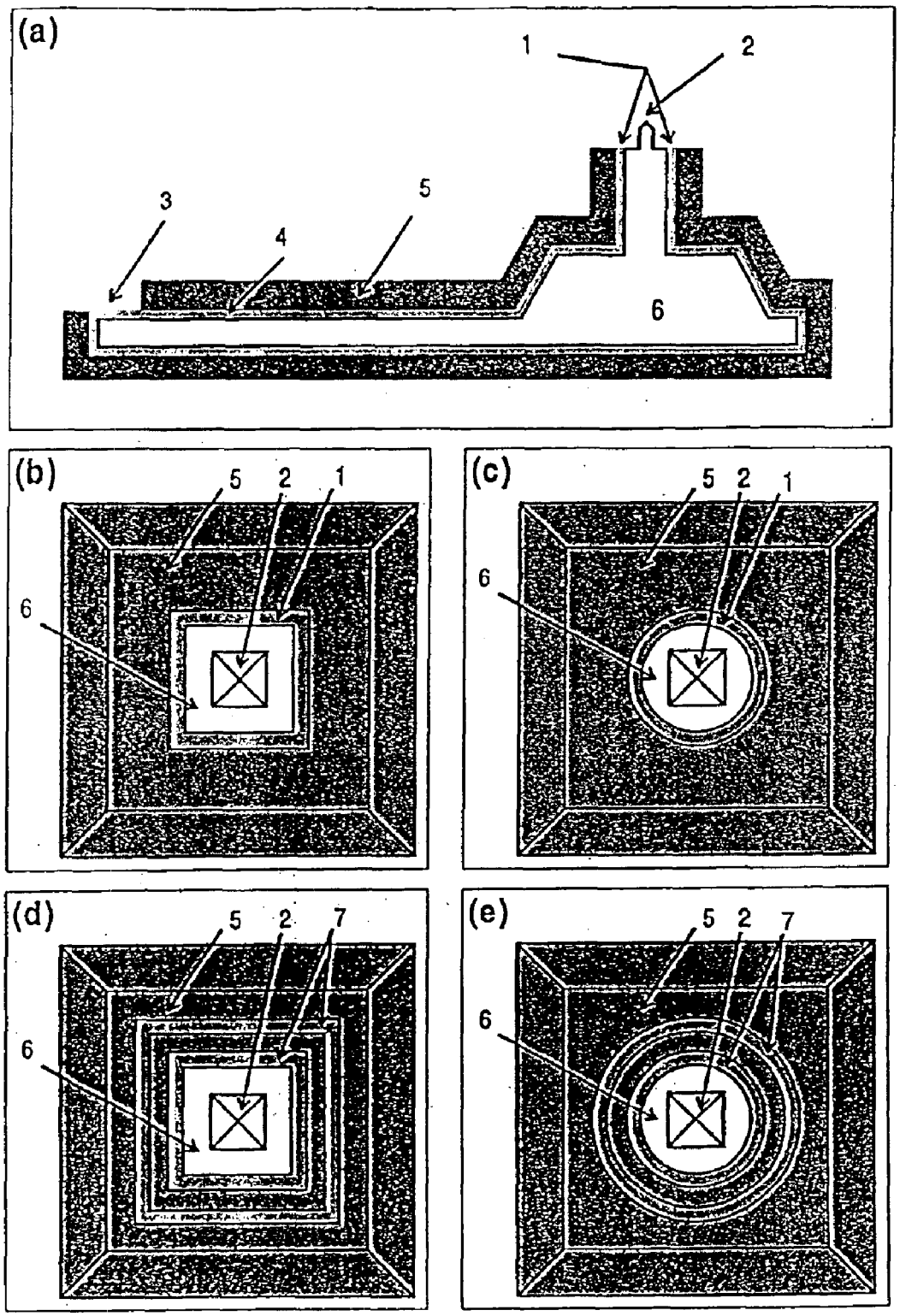
Figure 20:
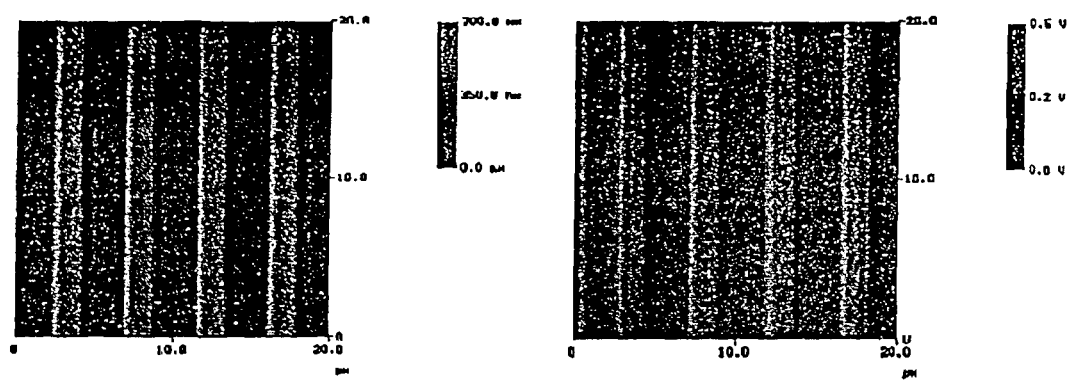

FIG. 10 shows a principle outline of the device according to the invention in schematic cross-section (a) and in a schematic perspective view (b);

FIG. 11 shows a principle outline to describe a production method for the device according to the invention;

FIG. 12 shows a principle outline to describe the production method for the device according to the invention in a view on the side face (a) and on the end face (b);

FIG. 13 shows a principle outline to describe the production method of the device according to the invention;

FIG. 14 shows a principle outline for the production method of the device according to the invention;

FIG. 15 shows a principle outline to describe the production method for the device according to the invention in multielectrode form; and FIG. 16 shows a principle outline for the inventive multielectrodes comprising an electrically conductive measurement tip;

FIG. 17 shows an embodiment having several individual tips arranged in parallel on a base body;

FIG. 18 shows an embodiment in form of a tip array;

FIG. 19 shows a schematic illustration of individual and multiple integrated frame/annular micro/nanoelectrodes; and FIG. 20 shows a combined AFM-SECM measurement with the measurement arrangement according to the invention.

EXAMPLES

Example 1
Production of the Near Field Probe with Integrated Ultramicroelectrode For the production, in the first step the cantilever and the glass body are coated with any desired electrode material, such as, e.g., gold. By using different coating times, the thickness of the electrode layer can be variably and reproducibly be made. By the plurality of the electrode materials available, the desired properties of the ultramicroelectrode can be adjusted, such as, e.g., the use of an antimony ultramicroelectrode for pH-sensitive measurements.

To electrically insulate the (electro)active area, the now coated cantilever is modified, e.g. with a silicon nitride layer. The application of the insulating layer is effected e.g. by aid of a plasma-enhanced chemical vapor deposition at a temperature of e.g. 300° C. and a gas mixture of $SiH_4$ and $NH_3$ in the pressure range of a few Torr and in the power range of a few 10 W power. The insulation may envelope the cantilever, yet it must at least completely insulate the conductive layer and during the measurements in liquid media it must be resistant to the solutions used. By using different coating times, the layer thickness of the nitride layer and thus, the degree of insulation can be fixed.

The uncovering of the (electro)active area is effected by methods of microstructur technology, such as, e.g., the focussed ion beam (FIB) technique. The tip of the cantilever can be milled such that a planar ultramicroelectrode, such as, e.g., a frame microelectrode, is produced. In the middle of this annular electrode, the original scanning near field tip is etched with the help of the FIB technique so that it will have a small, defined radius of curvature for the topographic imaging.

Figure 1:
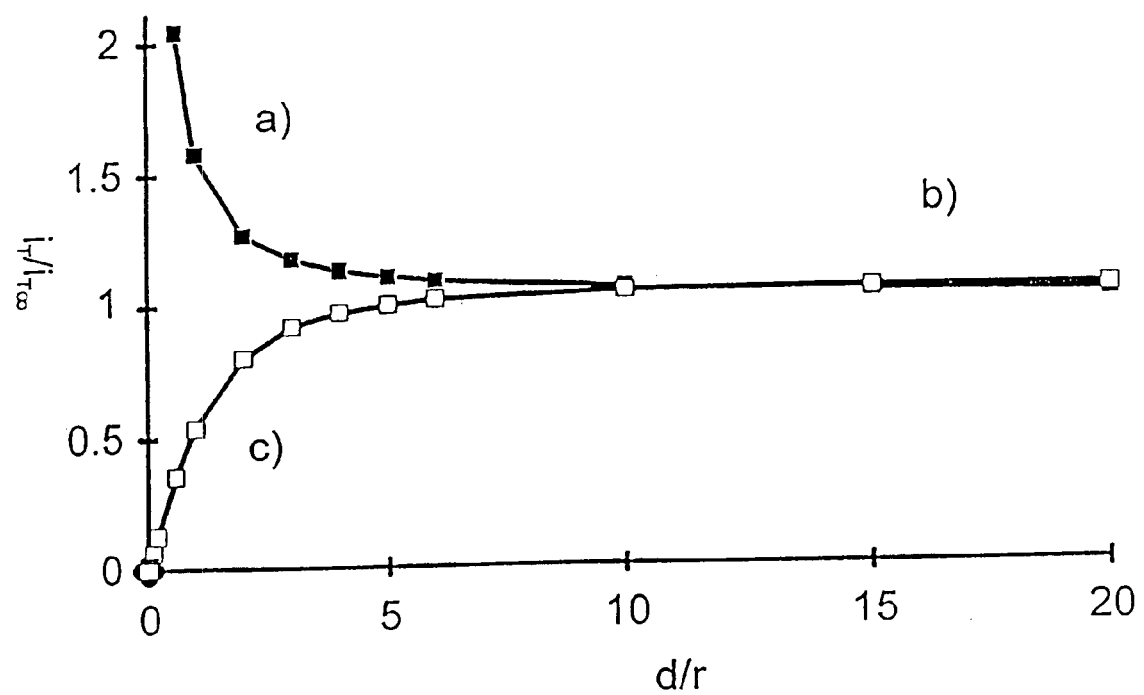
FIG. 1 shows calculated current-distance curves of microelectrodes when approaching a surface. Distance D is standardized to the radius R of the electrode, current $i_T$ is standardized to the current $i_{T\infty}$ of the non-influenced reaction. (a) Approach to a conductive substrate. (b) Region of the non-influenced reaction. (c) Approach to an insulator.
Figure 2:
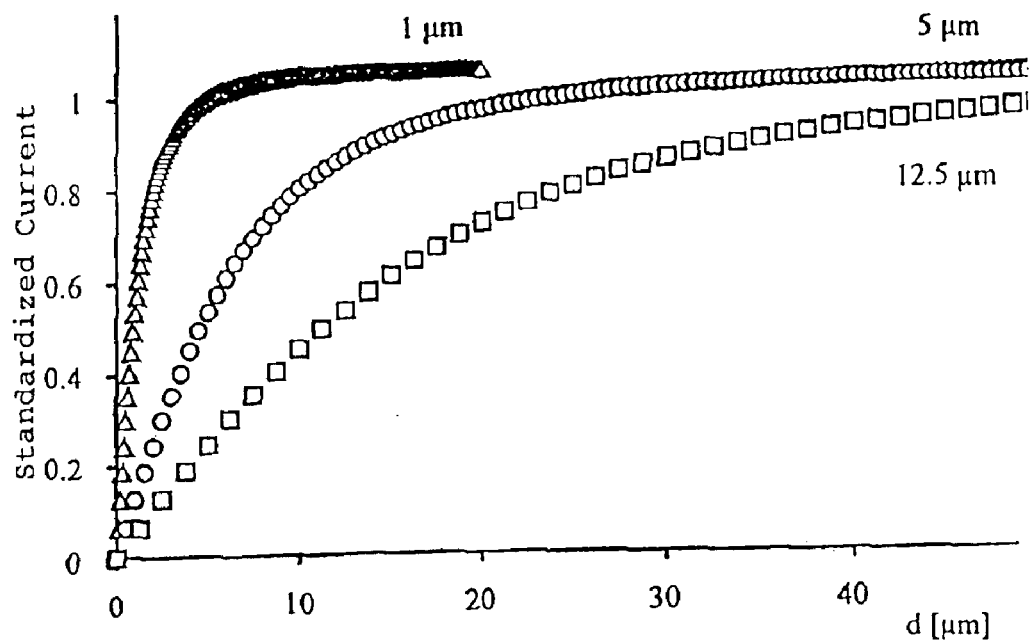
FIG. 2 shows the dependence of the working distance on the electrode size.
Figure 2:
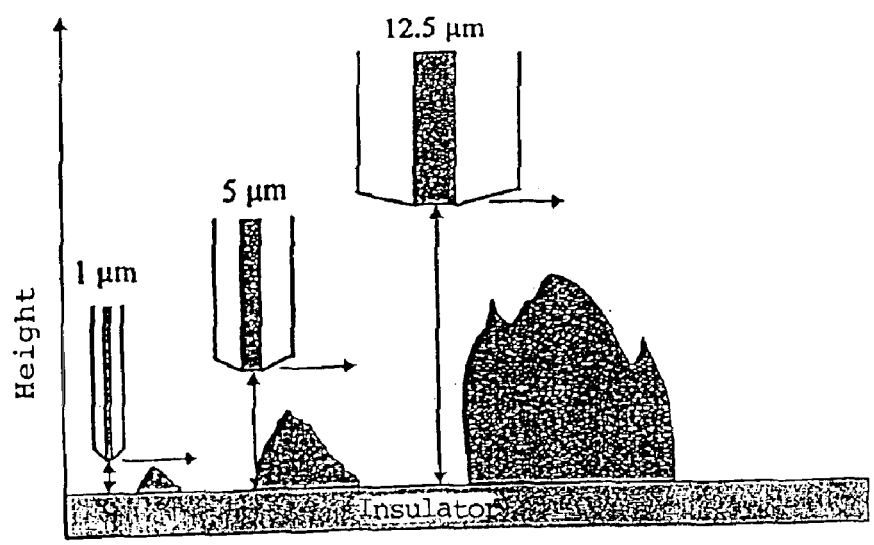
Figure 3:
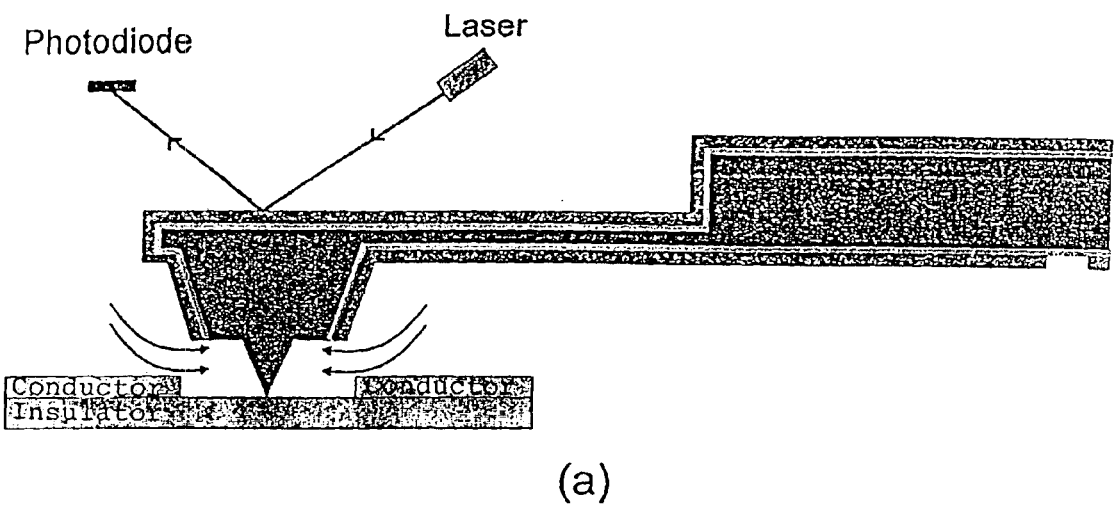
FIG. 3 shows (a) the schematic illustration of the distance control via the optic detection method and the diffusion limitation in the near field range by an insulating or chemically inert sample surface.
Figure 3:
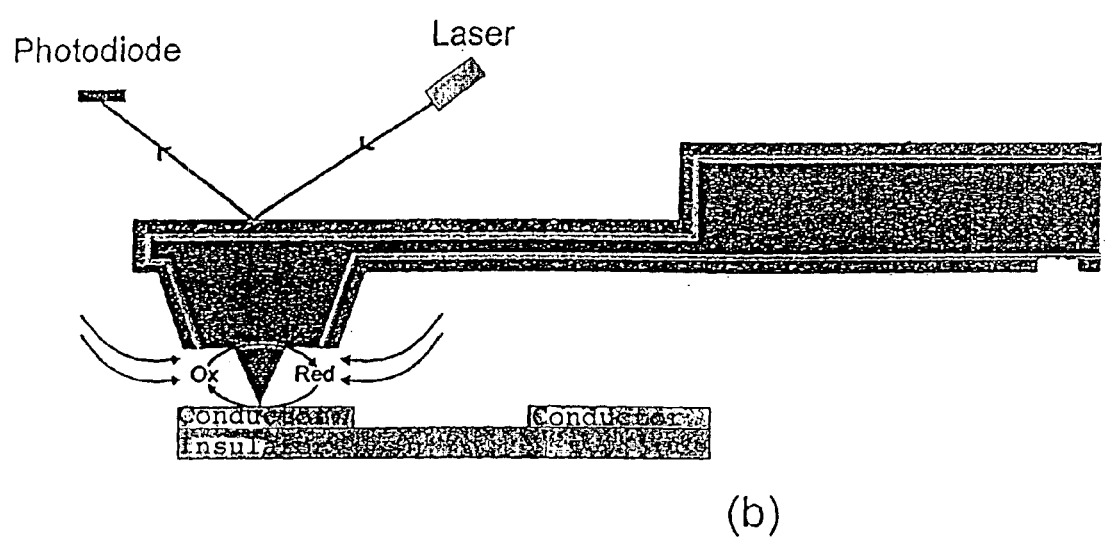

The length of the distance tip is now varied in correlation to the ultramicroelectrode radius so that the distance of the ultramicroelectrode will be in the sensitive working range to the sample (cf. FIG. 1). Since the working distance may fall below the radius of the microelectrode due to the controlled distance regulation, a further improvement of the resolution is attained (FIG. 3).

As an exemplary embodiment, the integrated scanning near field probe produced according to the invention, with an integrated ultramicroelectrode was installed in an AFM (FIG. 4).

For a near field probe according to the invention with a conductive core, the method described for a nonconductive core also applies accordingly, with the following modifications:
(i) applying an insulator layer on the conductive core;
(ii) applying a conductive layer;
(iii) applying an insulator layer once more;
(iv) uncovering again the original tip by means of a material-removing method.

For a near field probe according to the invention comprising a light-conductive core, such as, e.g., a fiber-optical light guide, the method described for a non-conductive core applies accordingly with the following modifications:
(i) applying a conductive layer;
(ii) applying an insulating layer;
(iii) uncovering the original tip again by means of a material-removing method.

The electrochemical properties of the scanning near field probes according to the invention and their applicability for local characterization as well as the quality of the individual manufacturing steps can be examined by electrochemical methods, such as, e.g., the cyclical voltammetry.

This is shown by way of example on an $Si_3N_4$ cantilever modified with 200 nm gold and an insulating layer of 800 nm $Si_3N_4$. At a mediator concentration of 10 mM in 0.1 M of potassium chloride, the cyclovoltammogram of the modified cantilever shows a leakage current of <1 pA (FIG. 5). Assuming that this is due to pinholes in the insulation, with the help of the theory of the stationary limiting current ($I_{T\infty}$):

$$I_{T\infty} = 4nFcDr \quad \text{(Equation 2)},$$

with: n: number of transmitted electrons, F: Faraday constant, D: diffusion coefficient, c: concentration, r: radius of the disk microelectrode, an (electro)active area of <0.01 $nm^2$ was determined on a disk electrode.

By way of example, by means of an integrated ultramicroelectrode in a non-conductive scanning near field probe having an (electro)active dimension of 100 nm diameter and an edge length of 2 μm, the theoretical diffusion limiting current is compared with the experimental data. With the help of equation 1, the diffusion limiting current of a micro-annular electrode can be correlated with the geometrical factors of the electrode, if a/b>0.9 (cf. W. R. Smythe, J. Appl. Phys., 22, 1499 (1951)):

$$I_d = nFDcI_o \quad \text{(Equation 3)}$$

$$I_o = \frac{\pi^2(a+b)}{\ln[16(a+b)/(b-a)]}$$

with: n: number of transmitted electrons, F: Faraday constant, D: diffusion coefficient, c: concentration, I: geometric factor of the annular microelectrode, a: inner radius, b: outer radius of the annular microelectrode.

For annular microelectrodes having any desired ratio of the inner to the outer radius of the electrode, the parameter $I_o$ can be described as follows (cf. A. Szabo, J. Phys. Chem., 91, 3108 (1987)):

$$I_o = \frac{\pi^2(a+b)}{\ln[32a(b-a) + \exp(\pi^2/4)]} \quad \text{(Equation 4)}$$

Assuming that the theoretical determination of the diffusion limiting current for annular microelectrodes also can be applied to this geometry, with a diffusion coefficient for potassium hexacyanoferrate (II) of $6.7 \cdot 10^{-6}$ cm$^2$/s for an inner radius of 0.95 $\mu$m and an outer radius of 1.1 $\mu$m, there results a diffusion limiting current of ~0.12 nA at a concentration of the redox mediator of c=5 mM. As is apparent from FIG. 6, the value calculated with the help of the dimensions of the annular microelectrode is in sufficient agreement with the measured value from the cyclovoltammogram, taking into consideration e.g. phenomenas, such as surface roughness and edge effects of the ultramicroelectrode. Since, in contrast to the approach by Macpherson et al., this is a planar microelectrode geometry, comparative statements regarding the dimensions of the (electro) active area can be made with the help of, e.g., the electron microscopy.

A prerequisite for the use of such integrated ultramicroelectrodes for characterizing surfaces is that the modification of the scanning near field tip does not impair the detection within the scope of the physical measurement principle. Therefore, AFM measurements were carried out with modified probes in air in the contact mode as an example. As the samples, both nearly planar structures of self-organizing monolayers on p-doped silicon platelets and also three-dimensional semiconductor structures were examined. The examination aimed at documenting the influence of the coating on the responding behavior of the cantilever (FIG. 7). By applying the conductive and the insulating layers, the geometry of the topographical imaging tip changes on account of the layer thicknesses. The original radius of curvature increases significantly. This can be shown by way of the image e.g. of a gold-GaAs grid having a periodicity of 3.4 mm. Since, however, in the method according to the invention, the original tip has been made by milling, this does not constitute a limitation of the method for the imaging quality of the scanning near field probe with integrated ultramicroelectrode.

The stability of the coatings applied was tested by way of AFM measurements in the contact mode (FIG. 8). This image shows by way of example the topography of polysiloxane islands on a p-doped silicon surface which had been recorded with a probe produced according to the invention. The measurement tip had a height of 2 $\mu$m and a radius of curvature of 300 nm. This is recognizable when compared with a non-modified AFM tip.

The stability of the ultramicroelectrode according to the invention was also shown by way of a gold-GaAS grid having a periodicity of 3.4 $\mu$m (FIG. 9).

For the use of force interactions between near field probe and mechanically instable samples, such as, e.g., in the examination of biological systems, a dynamic mode must be chosen for mapping the topography of the sample. In the tapping mode (dynamic mode, intermittent contact mode), the cantilever is stimulated with high frequency—in solution in a range of from 20 to 40 KHz—to an oscillation near the resonance frequency, and contacts the sample only at the point of the maximum amplitude of oscillation. In a first approximation, the oscillating cantilever can be described as a harmonic oscillator. The modulation of the scanning near field probe produces a modulation of the electrochemical measurement signal with the same frequency. By a suitable data recording and processing of the electrochemical measurement signal, the contribution produced by the oscillation of the scanning near field probe can be determined as a mean.

In the measurement tip according to the invention, the measurement tip (i) which serves to map the surface topography consists of $Si_3N_4$, yet by the present method it may also be produced of any material. Height and shape of the measurement tip can be varied. Typical dimensions—without restriction of the generality—are a height of 0.2 $\mu$m at a radius of curvature of the tips of <30 nm.

The geometry of the ultramicroelectrode may be controlledly varied in terms of shape and size. The distance of the electrode to the sample surface is adjusted by the height of the above-described measurement tip (i).

An insulating cover layer (iii), e.g. silicon nitride, covers the entire probe with the exception of the ultramicroelectrode, the connection area, and the measurement tip, and in the measurement tip according to the invention, this is, e.g. a nitride layer of a thickness of 900 nm which, preferably is applied by means of CVD. However, also any other insulation layer is possible which meets the requirements regarding insulation, flexibility and resistance to the media used during the measurement. This insulation layer must be sufficiently thick so as to guarantee the insulation, and sufficiently thin so as not to restrict the dynamic properties of the measurement tip.

Size and geometry (circular, elliptic, rectangular and also irregular electrode areas) of the electrically active area of the ultramicroelectrode can be produced and varied in controlled manner, just like the distance of the ultramicroelectrode from the surface and the relation of this distance to the electrically active area of the ultramicroelectrode.

The electrode jacket (insulating layer) is electrically insulating and chemically inert relative to the solutions used during measurement in liquid media.

The probe may advantageously be produced by the method according to the invention, as is described in more detail in the following. The production method illustrated in the enclosed principle outlines (FIGS. 11 to 14) substantially comprises the following steps:

The device according to the invention (probe) with an integrated ultramicroelectrode, in the examplary embodiment is based on base body at first in the form of an $Si_3N_4$ cantilever (FIG. 11(1)). Onto the latter, a conductive layer is applied, in the exemplary embodiment 200 nm of gold are sputtered thereon. The electrically conductive layer is covered with an insulating layer which must be resistant to the solutions used during measurements in liquid media (FIG. 11(3)). In the measurement tip according to the invention, e.g. a silicon nitride layer having a thickness of 900 nm has been deposited, e.g. by means of a plasma-supported CVD process.

In the next step, the outer insulating layer covering the electrode and a part of the electrode and of the base body is locally removed (regions indicated in broken lines in FIG. 12) by means of a material-removing method, preferably with a focussed ion beam arrangement, as illustrated in FIG. 12. This process is carried out once, from the side face (FIG. 12a) and once, offset by 90° thereto, from the end face (FIG. 12b).

From the remaining cuboid with the pyramid put thereupon and having the material sequence insulator-metal-insulator, a new measurement tip is formed, preferably by means of the focussed ion beam device as in the previous method step, by removing the regions indicated in broken lines in FIG. 13, once from the side face and once from the end face.

According to the invention, the measurement tip may be formed by a suitable selection of the material removal from the material of the base body (FIG. 13a), the conductive layer (FIG. 13b) or the insulating layer covering the metal (FIG. 13c). Illustrations d, e and f in FIG. 13 show the resultant tip configurations.

The height of the tip, the radius of the tip and the shape of the tip can also be varied by a suitable selection of the material removal. In the exemplary embodiment, the measurement tip consists of the material of the cantilever used.

Finally, the electrode areas in the exemplary embodiment are cleaned from re-deposited material by a special form of material removal with the FIB (single pass mill). In this single pass mill, the material-removing ion beam scans the regions indicated in FIG. 14 in broken lines just once, from top to bottom, so that finally the sample surface is sputtered by the ion beam just once and re-deposited material is removed thereby.

According to the invention, however, any other method that cleans the surface while maintaining the structure, such as, e.g., an etching process, may be used for cleaning the electrode areas.

Contacting the ultramicroelectrode may take place at any point desired, by locally removing the uppermost insulating layer by a structuring method and baring a respective connecting contact to the conductive layer.

In the above exemplary embodiment, contacting of the ultramicroelectrode is effected at the rear end of the glass body of the cantilever (FIG. 10).

From the method according to the invention, there result, e.g., the following possibilities of varying the electrode area or geometry, or the ratio of electrode area to the distance of the electrode from the sample surface and the lateral distance of the electrode from the measurement tip:

1. By applying electrically conductive layers of different thicknesses, the electrically active area of the probe can be varied independently of the pedestal height entered in FIG. 12.
2. With a fixed thickness of the electrically conductive layer, as is the case in the exemplary embodiment, with a pyramidal base body, the electrode areas can be diminished for greater pedestal heights (FIG. 12).
3. The geometry of the electrode can be varied by the choice of the base body on which the electrically conductive layer is applied. In the exemplary embodiment, a cantilever was used with whose pyramidal tip a square frame electrode results—as is apparent from FIG. 10. According to the invention, however, a base body of any desired shape may be used as the starting material, and thus, e.g., circular, elliptic, rectangular or polygonal electrodes can be realized. With the focussed ion beam device used in the exemplary embodiment, just as in any suitable structuring method, any desired—also irregular—shape of the base body can be provided, whereby it becomes possible to realize non-closed, in particular also segmented, ultramicroelectrodes.
4. The ratio electrode area/distance of the electrode to the sample surface can be varied by adjusting the height of the measurement tip.
5. The lateral distance of the microelectrode from the measurement tip for determining the surface topology may, as in the exemplary embodiment, be determined by the pedestal height (FIG. 12), with the base body having an appropriate shape.

In terms of number of layers and sequence of layers, the method according to the invention is not limited in any way. By an alternating coating of the insulating base body with conductive and insulating layers and, analogous to the exemplary embodiment, subsequent local removal of the material, thus also multielectrodes can be produced. The distances of the individual electrodes to the sample surface may vary. As an example, FIG. 15 shows an exemplary embodiment for a double electrode. For a probe according to the invention comprising several integrated electrodes, the method described will apply accordingly, with the modification that the material-removing step can be carried out twice with different pedestal heights (FIG. 15). The production of the measurement tip proper and the removal of redeposited material from the electrode are carried out analogously to the above-described exemplary embodiment.

If an electrically conductive material is used as the base body, a double electrode will be obtained by a series of structuring depositing and etching steps, with the measurement tip itself now being electrically conductive (FIG. 16).

In this case, any desired multilayer systems can be built up and thus, multielectrodes can be realized.

Any material may be used as the base body of the probe, in particular also fiber-optic guides and, generally, wave guides for electromagnetic waves. In this instance, e.g., a light beam (general electromagnetic waves) can be guided as far as to the probe tip and onto the sample. Moreover, also an external jacket layer may in this way be used as a wave guide or as a fiber-optic wave guide.

A further embodiment for the measurement methodology is possible by combining several measurement probes. This may be effected in the form of several individual tips arranged in parallel on a base body (FIG. 17) or in the form of an array of tips (FIG. 18).

In this instance, a plurality of measurement probes analyse in parallel individual regions of the sample, from which the total image of the sample surface can be provided by means of a data processing program. Depending on the number of measurement probes used, this will lead to a shortening of the measurement duration. A further variant is the simultaneous use of measurement probes of various types. For instance, ultramicroelectrodes having different electrode areas or electrode shapes, or also electrodes made of different materials or multielectrodes could simultaneously be used. Moreover, also the combination of measurement tips serving as microbiosensor, pH-sensitive or potentiometric ultramicroelectrode is possible, or ion-sensitive or ion-selective ultramicroelectrodes or any other near field microscopic analysis method can be combined with each other. When a signal is taken in case of a combination of measurement probes as illustrated in FIG. 17, care must be taken that such measurement probes are guided mutually decoupled. The taking of the measurement signal of each individual tip of a multielectrode array may, e.g., be effected via electrical lines guided on the webs of the array.

In FIG. 17, (1) denotes the base body with three integrated ultramicroelectrodes, (2) denotes the contact areas for signal taking, and (3) denotes the electrical parting line. In FIG. 18, (1) denotes an ultramicroelectrode array, (2) an individual multielectrode (may be of a different type), and (3) the webs of the multielectrode array.

In FIG. 19, a schematic illustration of individual and multiple integrated frame/annular micro/nanoelectrodes is given: (a) schematic sectional representation of an AFM cantilever after integration of the electrode and processing of the AFM tip; (b) integrated frame-micro/nano-electrode; (c) integrated annular micro/nano-electrode; (d) multiple integrated frame-micro/nano-electrodes; (e) multiple integrated annular micro/nano-electrodes. In FIG. 19, (1) denotes an integrated frame/annular micro/nano-electrode, (2) processed AFM tip, (3) electrical contact for signal taking, (4) conductive layer (e.g. gold), (5) electrically insulating layer, (6) original, untreated AFM cantilever and (7) multiple integrated frame/annular micro/nano-electrodes.

Example 2
Combined AFM-SECM Measurement with the Measurement Arrangement According to the Invention.

The combined measurement tip according to the invention was installed into a scanning force microscope from Digital (Nanoscope III). By way of example, gold webs on a gallium-arsenide wafer were examined. The gold webs have a periodicity of 4.3 $\mu$m and a height of 0.2 $\mu$m. The measurement was carried out in 0.5 mol/l KCl with a portion of 0.01 mol/l $[Fe(CN)_6]^{4-}$. The integrated annular gold electrode used in this example had an inner diameter of 900 nm. The shaped AFM tip was produced with a length of 1.5 $\mu$m.

Measurement parameters: imaging area 20 $\mu$m×20 $\mu$m; scan rate: 2 Hz; the measurement tip combined according to the invention was scanned from the left towards the right and from the top towards the bottom. The result is illustrated in FIG. 20: (left-hand side) topographic image of the surface with the AFM tip; (right-hand side) simultaneously recorded electrochemical image with the integrated electrode. A constant potential of +0.6 V (against an AgQRE (silver quasi-reference electrode)) was applied to the electrode.

What is claimed is:

1. A device capable of simultaneously carrying out electrochemical near field measurement and topographical near field measurement during use, the device comprising an arrangement comprising a region adapted for topographical near field measurement and a region for electrochemical near field measurement, wherein:
    the region for topographical near field measurement extends completely to an immediate tip of the arrangement;
    the region for electrochemical near field measurement starts a defined distance from the immediate tip;
    the region for topographical near field measurement is covered by a conductive material except for the immediate tip; and
    conductive material is covered by an insulating material except for the region for the electrochemical near field measurement.

2. The device of claim 1, further defined as comprising a scanning near field tip, which device, except for the immediate tip, is enveloped by a conductive material, which conductive material, with the exception of the region for electrochemical near field measurement, is covered by an insulating material.

3. The device of claim 1, wherein the region for electrochemical near field measurement has a thickness of from 10 to 2000 nm.

4. The device of claim 3, wherein the region for electrochemical near field measurement has a thickness of from 100 to 800 nm.

5. The device of claim 4, wherein the region for electrochemical near field measurement has a thickness of from 150 to 500 nm.

6. The device of claim 1, wherein the region for electrochemical near field measurement is comprised of a metal or metal alloy.

7. The device of claim 6, wherein the region for electrochemical near field measurement is comprised of gold, silver, platinum, palladium, tungsten, cadmium, aluminum, rhodium, iridium, copper, mercury alloys, a platinum-iridium-alloy, a platinum-rhodium-alloy, carbon, carbon electrode-glassy carbon, a high-order pyrolytic graphite (HOPG), a polysilicon, a doped polysilicon, a metal nitride, or a silicide.

8. The device of claim 7, wherein the region for electrochemical near field measurement is comprised of a metal nitride further defined as TiN or TaN.

9. The device of claim 8, wherein the conductive material is comprised of a silicide further defined as tungsten silicide or tantalum silicide.

10. The device of claim 1, further defined as a microbiosensor.

11. The device of claim 10, wherein the microbiosensor is further defined as an enzyme electrode, a pH-sensitive ultramicroelectrode, a potentiometric ultramicroelectrode, an ion-sensitive ultramicroelectrode, an ion-selective ultramicroelectrode, a potentiometric ultramicroelectrode, amperometric ultramicroelectrode, and/or a biomimetic ultramicroelectrode.

12. The device of claim 1, further defined as comprising a plurality of electrodes configured as multielectrodes and/or multisensors.

13. The device of claim 12, wherein measurement probes adapted for different measurement methods are provided.

14. The device of claim 1, wherein the defined distance of the region for near field measurement from the immediate tip is 0.5 $\mu$m to 100 nm.

15. The device of claim 14, wherein the defined distance of the region for near field measurement from the immediate tip is 1 $\mu$m to 50 nm.

16. The device of claim 15, wherein the defined distance of the region for near field measurement from the immediate tip is 2 $\mu$m to 30 nm.

17. A method for the ultramicroscopic examination of a surface comprising:
    obtaining a device capable of simultaneously carrying out an electrochemical and a topographical near field microscopy during use, the device comprising an arrangement comprising a region adapted for topographical near field measurement and a region for electrochemical near field measurement, wherein:
        the region for topographical near field measurement extends completely to an immediate tip of the arrangement;
        the region for electrochemical near field measurement starts a defined distance from the immediate tip;
        the region for topographical near field measurement is covered by a conductive material except for the immediate tip; and
        conductive material is covered by an insulating material except for the region for the electrochemical near field measurement;
    bringing the device into the vicinity of the surface to be examined so that both a distance to the surface can be measured by a topographical near field technique and also an electrochemical near field measurement of the surface can be carried out; and
    examining the surface by moving the device over the surface, with information obtained by the topographical near field technique being used to keep the device approximately at the same distance to the surface so that the electrochemical near field measurement is not impaired by topological fluctuations.

18. A near field microscope comprising:
    a device capable of simultaneously carrying out an electrochemical and a topographical near field microscopy during use, the device comprising an arrangement comprising a region adapted for topographical near field measurement and a region for electrochemical near field measurement, wherein:

the region for topographical near field measurement extends completely to an immediate tip of the arrangement;

the region for electrochemical near field measurement starts a defined distance from the immediate tip;

the region for topographical near field measurement is covered by a conductive material except for the immediate tip; and conductive material is covered by an insulating material except for the region for the electrochemical near field measurement;

an analysis unit in which measurements made by the device are recorded and processed during use;

the microscope adapted to transfer the electrochemical near field measurement from the device to the analysis unit and the topological near field measurement from the tip of the device to the analysis unit during use; and manipulating elements for the device that are controllable by the analysis unit during use.

19. The near field microscope of claim 18, further defined as comprising a force microscope.

* * * * *